United States Patent
Thomson et al.

(10) Patent No.: US 8,440,461 B2
(45) Date of Patent: May 14, 2013

(54) REPROGRAMMING SOMATIC CELLS USING RETROVIRAL VECTORS COMPRISING OCT-4 AND SOX2 GENES

(75) Inventors: James A. Thomson, Madison, WI (US); Junying Yu, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 644 days.

(21) Appl. No.: 12/053,440

(22) Filed: Mar. 21, 2008

(65) Prior Publication Data

US 2008/0233610 A1    Sep. 25, 2008

Related U.S. Application Data

(60) Provisional application No. 60/919,687, filed on Mar. 23, 2007, provisional application No. 60/974,980, filed on Sep. 25, 2007, provisional application No. 60/989,058, filed on Nov. 19, 2007.

(51) Int. Cl.
   *C12N 15/00* (2006.01)
(52) U.S. Cl.
   USPC ............................ 435/377; 435/384; 435/387
(58) Field of Classification Search ........................ None
   See application file for complete search history.

(56) References Cited

U.S. PATENT DOCUMENTS

| | | |
|---|---|---|
| 2002/0090722 A1 | 7/2002 | Dominko et al. |
| 2002/0136709 A1 | 9/2002 | Zhaner et al. |
| 2004/0199935 A1 | 10/2004 | Chapman |
| 2005/0255573 A1 | 11/2005 | Chambers et al. |
| 2006/0110830 A1 | 5/2006 | Dominko et al. |

FOREIGN PATENT DOCUMENTS

| | | |
|---|---|---|
| WO | 2007069666 A1 | 6/2007 |
| WO | 2008013737 A2 | 1/2008 |
| WO | 2008033469 A1 | 3/2008 |

OTHER PUBLICATIONS

Thomson et al. Embryonic Stem Cell Lines Derived from Human Blastocysts, Science, 1998, vol. 282, pp. 1145-1147.*
Cowan et al. Nuclear Reprogramming of Somatic Cells After Fusion with Human Embryonic Stem Cells Science, 2005, vol. 309, pp. 1369-1373.*
Taranger et al. Induction of Dedifferentiation, Genomewide Transcriptional Programming, and Epigenetic Reprogramming by Extracts of Carcinoma and Embryonic Stem Cells. Molec. Biol. Cell., 2005, vol. 16, pp. 5719-5735.*
Alberio et al. Reprogramming somatic cells into stem cells. Reproduction, 2006, vol. 132, pp. 709-720.*
Alberio R, et al., "Reprogramming somatic cells into stem cells," Reproduction 132:709-220 (2006).
Aoi T, et al., "Generation of Pluripotent Stem Cells from Adult Mouse Liver and Stomach Cells," Science Feb. 14, 2008 [Epub ahead of print].
Cibelli J, et al., "Cellular reprogramming for the creation of patient-specific embryonic stem cells," Stem Cell Rev. 2:289-295 (2006).
Collas P, "Dedifferentiation of cells: new approaches," Cytotherapy 9:236-244 (2007).
Egli D, et al., "Developmental reprogramming after chromosome transfer into mitotic mouse zygotes," Nature 447:679-685 (2007).
Fackler M, "Risk taking is in his genes," The New York Times, Dec. 11, 2007.
Hochedlinger K & Jaenisch R, "Nuclear reprogramming and pluripotency," Nature 441:1061-1067 (2006).
Ivanova I, et al. "Dissecting self-renewal in stem cells with RNA interference," Nature 442:533-538 (2006).
Maherali N, et al., "Directly reprogrammed fibroblasts show global epigenetic remodeling and widespread tissue contribution," Cell Stem Cell 1:55-70 (2007).
Masaki H, et al., "Heterogeneity of pluripotent marker gene expression in colonies generated in human iPS cell induction culture," Stem Cell Res. 1:105-115 (2005).
Meissner A, et al., "Direct reprogramming of genetically unmodified fibroblasts into pluripotent stem cells," Nat. Biotechnol. 25:1177-1181 (2007).
Nakagawa M, et al., "Generation of induced pluripotent stem cells without Myc from mouse and human fibroblasts," Nat. Biotechnol. 26:101-106 (2008).
Park I-H, et al., "Reprogramming of human somatic cells to pluripotency with defined factors," Nature 451:141-146 (2008).
Pralong D, et al., "Cell fusion for reprogramming pluripotency: toward elimination of the pluripotent genome," Stem Cell Rev. 2:331-340 (2006).
Silva J, et al., "Nanog promotes transfer of pluripotency after cell fusion," Nature 441:997-1001 (2006).
Takahasi K & Yamanaka S, "Induction of pluripotent stem cells from mouse embryonic and adult fibroblast cultures by defined factors," Cell 126:663-676 (2006).
Takahasi K, et al., "Induction of pluripotent stem cells from adult human fibroblasts by defined factors," Cell 131:861-872 (2007).
Wernig M, et al., "In vitro reprogramming of fibroblasts into a pluripotent ES-cell-like state," Nature 448:318-324 (2007).
Yamanaka S, "Strategies and new developments in the generation of patient-specific pluripotent stem cells," Cell Stem Cell 1:39-49 (2007).
Yu J, et al., "Human embryonic stem cells reprogram myeloid precursors following cell-cell fusion," Stem Cells 24:168-176 (2006).
Yu J, et al., "Induced pluripotent stem cell lines derived from human somatic cells," Science 318:1917-1920 (2007).
Xiang, Gao et al., "Nonviral Gene Delivery: What We Know and What is Next," The AAPS Journal 2007: 9(1), pp. E92-E104.
Frolov, Ilya et al., "Alphavirus-based expression vectors: Strategies and applications," Proc. Natl. Acad. Sci. USA, Vo. 93, pp. 11371-11377, Oct. 1996.
Wade-Martins, Richard et al., "Long-Term Stability of Large Insert Genomic DNA Episomeal Shuttle Vectors in Human Cells," Nucleic Acids Research, vol. 27, No. 7, pp. 1674-1682, 1999.
Milanesi, Gabriele et al., "BK virus-plasmid expression vector that persists episomally in human cells and shuttles into *Escherichia coli*," Molecular and Cellular Biology, pp. 1551-1560, Aug. 1984.
Ludwig, Tenneille et al., "Derivation of Human Embryonic Stem Cells in Defined Conditions," Nature Biotechnology, vol. 24 No. 2, pp. 185-187, Feb. 2006.

\* cited by examiner

*Primary Examiner* — Deborah Crouch
(74) *Attorney, Agent, or Firm* — Quarles & Brady LLP

(57) ABSTRACT

The present invention relates to methods for reprogramming a somatic cell to pluripotency by administering into the somatic cell at least one or a plurality of potency-determining factors. The invention also relates to pluripotent cell populations obtained using a reprogramming method.

9 Claims, 16 Drawing Sheets

A.

B.

REPROGRAMMING SOMATIC CELLS USING RETROVIRAL VECTORS COMPRISING OCT-4 AND SOX2 GENES

CROSS-REFERENCE TO RELATED APPLICATIONS

This application claims the benefit of U.S. Provisional Patent Application No. 60/919,687, filed Mar. 23, 2007; U.S. Provisional Patent Application No. 60/974,980, filed Sep. 25, 2007; and U.S. Provisional Patent Application No. 60/989,058, filed Nov. 19, 2007, each of which is incorporated herein by reference as if set forth in its entirety.

STATEMENT REGARDING FEDERALLY SPONSORED RESEARCH OR DEVELOPMENT

This invention was made with United States government support awarded by the following agencies: NIH R000167, GM069981. The United States government has certain rights in this invention.

BACKGROUND

Embryonic stem (ES) cells can grow indefinitely while maintaining pluripotency and can differentiate into cells of all three germ layers (Evans & Kaufman, Nature 292:154-156 (1981)). Human ES cells will be useful in treating a host of diseases, such as Parkinson's disease, spinal cord injury and diabetes (Thomson et al., Science 282:1145-1147 (1998)). Scientists have sought technical solutions to avoid the current method of generating ES cells from blastocyst cells and to avoid anticipated tissue rejection problems following transplantation into patients. One desirable way to accomplish these solutions would be to generate pluripotent cells directly from somatic cells of a post-natal individual.

Somatic cells can be reprogrammed by transferring their nuclear contents into oocytes (Wilmut et al, Nature 385:810-813(1997)) or by fusion with ES cells (Cowan et al., Science 309:1369-1373 (2005)), indicating that unfertilized eggs and ES cells contain factors that confer totipotency or pluripotency in somatic cells.

Likewise, Yu et al. showed that cells derived by in vitro differentiation from an H1 Oct4 knock-in ES cells did not express EGFP, but that EGFP expression was restored upon cell-cell fusion with human ES cells. Yu et al., Stem Cells 24:168-176 (2006), incorporated herein by reference as if set forth in its entirety). Therefore, Yu et al. demonstrated that differentiated cells can become pluripotent via cell-cell fusion with human ES cells. Regardless of the differentiated cell type, upon fusion with undifferentiated human ES cells, ES cell specific antigens and marker genes were expressed and differentiation-specific antigens were no longer detectable in the fused hybrid cells. Advantageously, EGFP expression was re-established in the hybrid cells, providing a convenient marker for re-establishment of pluripotent stem cell status. When the hybrid cells formed embryoid bodies (EBs), genes characteristic of all three germ layers and extra-embryonic tissues were up-regulated, indicating that the hybrid cells had a potential to differentiate into multiple lineages.

Although the transcriptional determination of pluripotency is not fully understood, several transcription factors, including Oct 3/4 (Nichols et al., Cell 95:379-391(1998)), Sox2 (Avilion et al., Genes Dev. 17:126-140 (2003)) and Nanog (Chambers et al., Cell 113:643-655(2003)) are involved in maintaining ES cell pluripotency; however, none is sufficient alone to specify ES cell identity.

Chambers & Smith (EP 1 698 639 A2, (2002)) maintained pluripotent murine cells without a feeder layer or feeder cell extract and without a gp 130 cytokine by introducing vectors that encode or activate differentiation-suppressing factors, but did not convert differentiated cells into a pluripotent state.

More recently, Takahashi & Yamanaka introduced four factors (i.e., Oct3/4, Sox2, c-Myc and Klf4) into mouse ES cells and mouse adult fibroblasts cultured under conditions suitable for mouse ES cell culture to obtain induced pluripotent stem (iPS) cells that exhibited mouse ES cell morphology and growth properties and expressed mouse ES cell marker genes (Takahashi & Yamanaka, Cell 126:663-676 (2006)). Notably, exogenous Oct-4 introduced into the mouse fibroblasts resulted in only marginal Oct-4 expression. Subcutaneous transplantation of iPS cells into nude mice resulted in tumors containing a variety of tissues from all three germ layers. Following injection into blastocysts, iPS cells contributed to mouse embryonic development. However, c-Myc, which was necessary for pluripotent induction, is an oncogene. Likewise, Klf4 is an oncogene. These data demonstrate that pluripotent cells can be directly generated from mouse fibroblast cultures by adding only a few defined factors using a retroviral transduction. However, as described infra, the set of factors used to produce iPS cells from differentiated mouse cells was insufficient to reprogram human somatic cells to pluripotency using lentiviral vectors without introducing additional changes to the cells.

One could hypothesize that factors that can reprogram human somatic cells differ from those factors that can reprogram somatic cells from model organisms (including mice) because ES cells from mice and humans require distinct sets of factors to remain undifferentiated, illustrating the significance of species-specific differences, even among mammals. For example, the leukemia inhibitory factor (LIF)/Stat3 pathway, a key to mouse ES cell proliferation, does not support human ES cell proliferation and appears inactive in conditions that support human ES cells (Daheron L, et al., Stem Cells 22:770-778 (2004); Humphrey R, et al., Stem Cells 22:522-530 (2004); and Matsuda T, et al., EMBO J. 18:4261-4269 (1999)).

Similarly, while bone morphogenetic proteins (BMPs) together with LIF support mouse ES cell self-renewal at clonal densities in serum-free medium (Ying Q, et al., Cell 115:281-292 (2003)), they cause rapid human ES cell differentiation in conditions that would otherwise support self-renewal, such as culture on fibroblasts or in fibroblast-conditioned medium (Xu R, et al., Nat. Biotechnol. 20:1261-1264 (2002)). Indeed, inhibition of BMP signaling in human ES cells is beneficial (Xu R, et al., Nat. Methods 2:185-190 (2005)).

Still further, fibroblast growth factor (FGF) signaling is important to self-renewal of human ES cells, but apparently not for mice (Xu et al., (2005), supra; and Xu C, et al., Stem Cells 23:315-323 (2005)).

Accordingly, the art still seeks a set of potency-determining factors suited at least for use in methods for reprogramming primate (including human and non-human) somatic cells to yield pluripotent cells. Such cells, obtained without relying upon embryonic tissues, would be suited for use in applications already contemplated for existing, pluripotent, primate ES cells.

BRIEF SUMMARY

The present invention is broadly summarized as relating to methods for reprogramming differentiated, somatic, primate cells into pluripotent cells, and more specifically into iPS cells. As used herein, "iPS cells" refer to cells that are substantially genetically identical to their respective differentiated somatic cell of origin and display characteristics similar to higher potency cells, such as ES cells, as described herein. The cells can be obtained from various differentiated (i.e., non-pluripotent and multipotent) somatic cells.

iPS cells exhibit morphological (i.e., round shape, large nucleoli and scant cytoplasm) and growth properties (i.e., doubling time; ES cells have a doubling time of about seventeen to eighteen hours) akin to ES cells. In addition, iPS cells express pluripotent cell-specific markers (e.g., Oct-4, SSEA-3, SSEA-4, Tra-1-60, Tra-1-81, but not SSEA-1). iPS cells, however, are not immediately derived from embryos and can transiently or stably express one or more copies of selected potency-determining factors at least until they become pluripotent. As used herein, "not immediately derived from embryos" means that the starting cell type for producing iPS cells is a non-pluripotent cell, such as a multipotent cell or terminally differentiated cell, such as somatic cells obtained from a post-natal individual.

In the methods described herein, at least two potency-determining factors can be introduced into, and expressed in, differentiated somatic cells, whereupon the somatic cells convert in culture to cells having properties characteristic of pluripotent cells, such as human ES cells (i.e., express at least Oct-4, SSEA-3, SSEA-4, TRA-1-60 or TRA-1-81, but not SSEA-1, and appear as compact colonies having a high nucleus to cytoplasm ratio and prominent nucleolus), that can differentiate into cells characteristic of all three germ layers, and that contain the genetic complement of the somatic cells of a post-natal individual. Apart from genetic material introduced to encode the potency-determining factors, the reprogrammed (i.e., converted) cells are substantially genetically identical to the somatic cells from which they were derived.

As used herein, a "potency-determining factor" refers to a factor, such as a gene or other nucleic acid, or a functional fragment thereof, as well as an encoded factor or functional fragment thereof, used to increase the potency of a somatic cell, so that it becomes pluripotent. The potency-determining factors optionally can be present only transiently in the reprogrammed cells or can be maintained in a transcriptionally active or inactive state in the genome of the reprogrammed cells. Likewise, the potency-determining factors can be present in more than one copy in the reprogrammed cells, where the potency-determining factor can be integrated in the cell's genome, can be extra-chromosomal or both. The potency-determining factors can include, but are not limited to, Stella (SEQ ID NO:1); POU5F1 (Oct-4; SEQ ID NO:2), Sox2 (SEQ ID NO:3), FoxD3, UTF1, Rex1, ZNF206, Sox15, Myb12, Lin28 (SEQ ID NO:4), Nanog (SEQ ID NO:5), DPPA2, ESG1, Otx2 and subsets thereof. In some embodiments, as few as two potency-determining factors, e.g., Oct-4 and Sox2, can be sufficient. Efficiency in obtaining reprogrammed cells, however, can be improved by including additional potency-determining factor, such as Lin28, Nanog or both.

In a first aspect, the invention relates to a replenishable, enriched population of pluripotent cells obtained from a post-natal individual, especially from a living individual, but optionally from a deceased individual. Cells in the enriched cell population express at least one cell-type-specific marker, including, but not limited to, Oct-4, SSEA3, SSEA4, Tra-1-60, Tra-1-81 or combinations thereof and have other hallmarks of pluripotent cells, such as ES cells. In addition, the pluripotent cells may express alkaline phosphatase (ALP). Furthermore, the pluripotent cells may have a genome substantially genetically identical to that of a pre-existing, differentiated cell from the individual. Likewise, the pluripotent cells may have a genome that encodes at least one of the potency-determining factors, which may be transcriptionally active or inactive after reprogramming. Additionally, the potency-determining factors may be in a form of a reprogramming sequence in which a polynucleotide encoding the potency-determining factor is operably linked to a heterologous promoter. As used herein, "heterologous promoter" means a promoter that is operably linked to a polynucleotide for which the promoter does not normally initiate transcription.

In a second aspect, the invention relates to methods and compositions for identifying potency-determining factors required to reprogram somatic cells into pluripotent cells.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages and features of the present invention will become apparent from the following specification taken in conjunction with the accompanying drawings.

BRIEF DESCRIPTION OF THE SEVERAL VIEWS OF THE DRAWINGS

FIG. 2A shows schematics of myeloid precursor derivation and purification from human ES cells. FIG. 2B shows phenotypic analysis of differentiated cells obtained after Percoll® separation. Gray line: isotype control; black line: antibody staining. Abbreviations: hESC, human embryonic stem cell; MPO, myeloperoxidase; pHEMA, poly(2-hydroxyethyl methacrylate).

FIG. 4A shows a schematic diagram of lentiviral construct. FIG. 4B shows Percoll®-purified cells were transduced with EGFP-expressing lentiviral vectors at various MOI. EGFP expression was analyzed by flow cytometry three days after transduction without drug selection. FIG. 4C shows lentiviral transduction of Percoll®-purified cells after several additional days of culture on Matrigel®. EGFP expression was analyzed two days after lentiviral transduction.

FIG. 6A shows the established clones display undifferentiated human ES cell morphology and express EGFP under direction of the endogenous Oct4 promoter. FIG. 6B shows flow cytometry analysis of human ES cell-specific cell surface antigen expression in established clones. Gray line: isotype control; black line: antibody staining.

FIG. 7A shows the identified set of fourteen potency-determining factors was introduced into cells in combinations, wherein each combination excluded one of the fourteen factors. By evaluating the ability of the potency-determining factors to reprogram the tested cells to an ES-like state, the inventors determined whether the excluded potency-determining factor was essential to the reprogramming. For example, a set of potency-determining factors termed M1 that lacked Oct-4 (depicted as M1-Oct-4) was unable to form a significant number of ES-like colonies. As such, it was concluded that Oct-4 was important for somatic cell reprogramming. FIG. 7B shows a set of potency-determining factors (narrowed from FIG. 7A) evaluated for further testing was narrowed from fourteen to four (M4, being Oct-4, Sox2, Lin28 and Nanog). These four potency-determining factors were tested by serially excluding one of the four from the combination. Where a combination of three potency-determining factors (e.g., M4-Oct-4) was unable to reprogram the tested cells to form a significant number of stable ES-like colonies, the inventors concluded that the omitted gene is important for somatic cell reprogramming. In FIG. 7B, the light gray bars indicate the total number of reprogrammed colonies formed having typical human ES cell morphology; dark gray bars indicate the number of large colonies with minimal differentiation. FIG. 7C shows a set of potency-determining factors (narrowed from FIG. 7B) evaluated for further testing was narrowed from four to two (i.e., Oct-4 and Sox2). Oct-4, Sox2, Lin28 and Nanog were tested by serially excluding two of the four from the combination.

FIG. 8A shows bright-field images of human adult skin cell (p5) (left) and reprogrammed cells (right). FIG. 8B shows flow cytometry analysis of human ES cell-specific markers in human adult skin cells (p5) (bottom) and reprogrammed cells (top). Gray line: isotype control; black line: antibody staining.

FIG. 9A shows Western blot analysis of Oct-4 and Sox2 in 293FT cells; lane 1, pSin4-EF2-Oct4-IRES1-Sox2 (OS-IRES1); lane 2, pSin4-EF2-Oct4-IRES2-Sox2 (OS-IRES2); lane 3, pSin4-EF2-Oct4-F2A-Sox2 (OS-F2A); lane 4, pSin4-EF2-Oct4-IRES1-puro (O); lane 5, pSin4-EF2-Sox2-IRES1-puro (S); lane 6, no plasmid (control). FIG. 9B shows reprogramming in mesenchymal cells derived from OCT4 knock-in human ES cells using linked potency-determining factors; gene combinations are the same as in FIG. 9A, with the addition of pSin4-EF2-Nanog-IRES1-puro (N) and pSin4-EF2-Lin28-IRES1-puro (L).

DETAILED DESCRIPTION OF PREFERRED EMBODIMENTS

Figure 1:
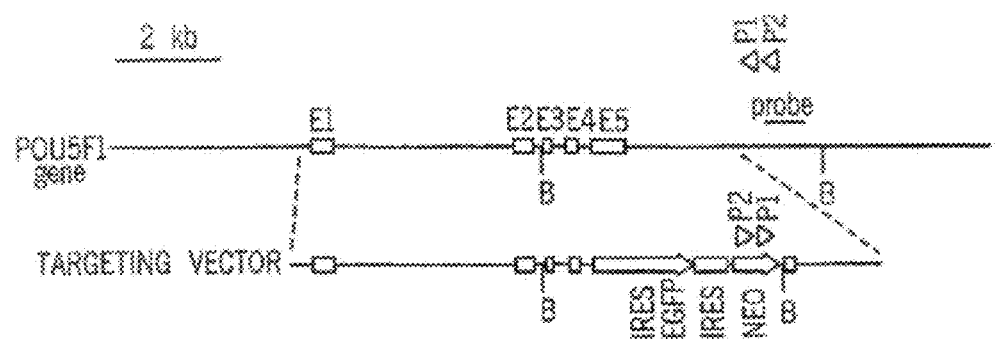
FIG. 1 illustrates a site downstream from a human Oct4 promoter into which a knock-in construct was introduced. In cells containing the knock-in construct, enhanced green fluorescent protein (EGFP) and neomycin phosphotransferase (NEO) are expressed when the Oct4 promoter is active. These cells can be used to evaluate which factors can reprogram somatic cells into pluripotent cells.

The inventors hypothesized that potency-determining factors present in primate ES cells play an important role in maintaining pluripotency and that differentiated somatic cells could be reprogrammed to a state of pluripotency through expression of potency-determining factors.

Cell types pass through various levels of potency during differentiation, such as totipotency, pluripotency and multipotency. Of particular interest herein are pluripotent cells. As used herein, "pluripotent cells" refer to a population of cells that can differentiate into all three germ layers (e.g., endoderm, mesoderm and ectoderm). Pluripotent cells express a variety of pluripotent cell-specific markers, have a cell morphology characteristic of undifferentiated cells (i.e., compact colony, high nucleus to cytoplasm ratio and prominent nucleolus) and form teratomas when introduced into an immunocompromised animal, such as a SCID mouse. The teratomas typically contain cells or tissues characteristic of all three germ layers. One of ordinary skill in the art can assess these characteristics by using techniques commonly used in the art. See, e.g., Thomson et al., supra. Pluripotent cells are capable of both proliferation in cell culture and differentiation towards a variety of lineage-restricted cell populations that exhibit multipotent properties. Multipotent somatic cells are more differentiated relative to pluripotent cells, but are not terminally differentiated. Pluripotent cells therefore have a higher potency than multipotent cells. As used herein, "reprogrammed pluripotent primate stem cells" (and similar references) refer to the pluripotent products of somatic cell reprogramming methods. Such cells are suitable for use in research and therapeutic applications currently envisioned for human ES cells.

The present invention broadly relates to novel methods for reprogramming differentiated somatic cells into higher-potency cells, such as pluripotent cells, by administering at least two potency-determining factors into somatic cells to achieve a higher level of potency in the reprogrammed cells than in the somatic cells. Advantageously, the present invention allows the generation of pluripotent cells, such as iPS cells, from somatic cells without requiring an addition of cell surface receptors for introducing the potency-determining factors to the somatic cells. As used herein, "reprogramming" refers to a genetic process whereby differentiated somatic cells are converted into de-differentiated, pluripotent cells, and thus have a greater pluripotency potential than the cells from which they were derived. That is, the reprogrammed cells express at least one of the following pluripotent cell-specific markers: SSEA-3, SSEA-4, TRA-1-60 or TRA 1-81. Preferably, the reprogrammed cells express all these markers.

Potency-determining factors that can reprogram somatic cells include, but are not limited to, factors such as Oct-4, Sox2, FoxD3, UTF1, Stella, Rex1, ZNF206, Sox15, Myb12, Lin28, Nanog, DPPA2, ESG1, Otx2 or combinations thereof. In the examples, a set with as few as two of the fourteen factors was sufficient to reprogram the tested cells; this set included Oct-4 and Sox2. Addition of other potency-determining factors to Oct-4 and Sox2, however, increased the efficiency with which reprogrammed cells were obtained. c-Myc and Klf4, however, are not essential as potency-determining factors. Preferably, the potency-determining factor may be a transcription factor.

Suitable somatic cells can be any somatic cell, although higher reprogramming frequencies are observed when the starting somatic cells have a doubling time about twenty-four hours. Somatic cells useful in the invention are non-embryonic cells obtained from a fetal, newborn, juvenile or adult primate, including a human. Examples of somatic cells that can be used with the methods described herein include, but are not limited to, bone marrow cells, epithelial cells, fibroblast cells, hematopoietic cells, hepatic cells, intestinal cells, mesenchymal cells, myeloid precursor cells and spleen cells. Another type of somatic cell is a $CD29^+$ $CD44^+$ $CD166^+$ $CD105^+$ $CD73^+$ and $CD31^-$ mesenchymal cell that attaches to a substrate. Alternatively, the somatic cells can be cells that can themselves proliferate and differentiate into other types of cells, including blood stem cells, muscle/bone stem cells, brain stem cells and liver stem cells. Multipotent hematopoietic cells, suitably myeloid precursor or mesenchymal cells, are specifically contemplated as suited for use in the methods of the invention.

Likewise, suitable somatic cells are receptive, or can be made receptive using methods generally known in the scientific literature, to uptake of potency-determining factors including genetic material encoding the factors. Uptake-enhancing methods can vary depending on the cell type and expression system. Exemplary conditions used to prepare receptive somatic cells having suitable transduction efficiency are known in the art and are described in the examples below. One method for making cells receptive to potency-determining factors is described below in connection with the electroporation methods.

A potency-determining factor may be introduced as a reprogramming sequence in which a polynucleotide sequence encoding the potency-determining factor is operably linked to a heterologous promoter, which may become inactive after somatic cells are reprogrammed. The heterologous promoter is any promoter sequence that can drive expression of a polynucleotide sequence encoding the potency-determining factor in the somatic cell, such as, e.g., an Oct4 promoter.

The relative ratio of potency-determining factors may be adjusted to increase reprogramming efficiency. For example, linking Oct-4 and Sox2 in a 1:1 ratio on a single vector increased reprogramming efficiency in cells by a factor of four (FIG. 9A-B) when compared to reprogramming efficiency wherein the potency-determining factors were provided to cells in separate constructs and vectors, where the uptake ratio of the respective potency-determining factors into single cells was uncontrolled. Although the ratio of potency-determining factors may differ depending upon the set of potency-determining factors used, one of ordinary skill in possession of this disclosure can readily determine an optimal ratio of potency-determining factors.

Pluripotent cells can be cultured in any medium used to support growth of pluripotent cells. Typical culture medium includes, but is not limited to, a defined medium, such as TeSR™ (StemCell Technologies, Inc.; Vancouver, Canada), mTeSR™ (StemCell Technologies, Inc.) and StemLine® serum-free medium (Sigma; St. Louis, Mo.), as well as conditioned medium, such as mouse embryonic fibroblast (MEF)-conditioned medium. As used herein, a "defined medium" refers to a biochemically defined formulation comprised solely of biochemically-defined constituents. A defined medium may also include solely constituents having known chemical compositions. A defined medium may further include constituents derived from known sources. As used herein, "conditioned medium" refers to a growth medium that is further supplemented with soluble factors from cells cultured in the medium. Alternatively, cells can be maintained on MEFs in culture medium.

The inventors used a serial analysis of gene expression (SAGE) library to obtain transcriptome profiles of genes abundant in ES cells. Specifically, a SAGE library was used to identify potency-determining factors that regulate pluripotency and self-renewal in ES cells. SAGE libraries are well-known to one of ordinary skill in the art and are publicly available or can be specifically constructed by companies, such as Agencourt Bioscience Corp. (Beverly, Mass.).

In another aspect, the invention provides an enriched population of pluripotent cells substantially genetically identical to cells of a post-natal individual. The cells can be obtained by reprogramming somatic cells isolated from the post-natal individual. In some embodiments, the cell population is a purified population, representing at least 60%, 70%, 80% and advantageously greater than 95% of the cells in the population, and any and all whole or partial integers therebetween. The reprogrammed cells are euploid, exhibit cell morphology characteristic of pluripotent cells and express pluripotent cell-specific markers, such as, e.g., Oct-4, SSEA-3, SSEA-4, Tra-1-60, Tra-1-81 or combinations thereof, and form teratomas when introduced into an immunocompromised animal.

Yet another aspect provides methods and compositions for identifying and using potency-determining factors sufficient to reprogram somatic cells into pluripotent cells. As noted herein, the reprogrammed pluripotent cells contain the genetic complement of, and are substantially genetically identical to somatic cells obtained from a post-natal individual. Generally, methods for identifying potency-determining factors include the steps of introducing genetic material encoding one or a plurality of putative potency-determining factors into somatic cells receptive to uptake of the genetic material under conditions effective to express the factors encoded on the introduced genetic material at levels sufficient to reprogram the cells to a less differentiated, higher-potency state; and observing a population of pluripotent cells after introduction of the genetic material. The pluripotent cells can be characterized by cell morphology, pluripotent cell-specific markers or both. Advantageously, the pluripotent cells can be identified by expression in the treated cells of a marker provided in the cells so as to be expressed only upon reprogramming of the cells to a pluripotent state. Through this approach, potency-determining factors capable of reprogramming somatic cells into pluripotent cells can be identified, as is described in the examples below.

Genetic material encoding a potency-determining factor can be introduced by transfection or transduction into the somatic cells using a vector, such as an integrating- or non-integrating vector. Of particular interest herein are retroviral vectors. Retroviral vectors, particularly lentiviral vectors, are transduced by packaging the vectors into virions prior to contact with a cell. After introduction, the DNA segment(s) encoding the potency-determining factor(s) can be located extra-chromosomally (e.g., on an episomal plasmid) or stably integrated into cellular chromosome(s).

A viral-based gene transfer and expression vector is a genetic construct that enables efficient and robust delivery of genetic material to most cell types, including non-dividing and hard-to-transfect cells (primary, blood, stem cells) in vitro or in vivo. Viral-based constructs integrated into genomic DNA result in high expression levels. In addition to a DNA segment that encodes a potency-determining factor of interest, the vectors include a transcription promoter and a polyadenylation signal operatively linked, upstream and downstream, respectively, to the DNA segment. The vector can include a single DNA segment encoding a single potency-determining factor or a plurality of potency-determining factor-encoding DNA segments. A plurality of vectors can be introduced into a single somatic cell. The vector can optionally encode a selectable marker to identify cells that have taken up and express the vector. As an example, when the vector confers antibiotic resistance on the cells, antibiotic can be added to the culture medium to identify successful introduction of the vector into the cells. Integrating vectors can be employed, as in the examples, to demonstrate proof of concept. Retroviral (e.g., lentiviral) vectors are integrating vectors; however, non-integrating vectors can also be used. Such vectors can be lost from cells by dilution after reprogramming, as desired. A suitable non-integrating vector is an Epstein-Barr virus (EBV) vector. Ren C, et al., Acta. Biochim. Biophys. Sin. 37:68-73 (2005); and Ren C, et al., Stem Cells 24:1338-1347 (2006), each of which is incorporated herein by reference as if set forth in its entirety.

The vectors described herein can be constructed and engineered using art-recognized techniques to increase their safety for use in therapy and to include suitable expression elements and therapeutic genes. Standard techniques for the construction of expression vectors suitable for use in the present invention are well-known to one of ordinary skill in the art and can be found in such publications such as Sambrook J, et al., "Molecular cloning: a laboratory manual," (3rd ed. Cold Spring Harbor Press, Cold Spring Harbor, N.Y. 2001), incorporated herein by reference as if set forth in its entirety.

The ability to identify and enrich for pluripotent cells can be facilitated by providing a non-lethal marker in the somatic cells, such as Green Fluorescent Protein (GFP), Enhanced Green Fluorescent Protein (EGFP) or luciferase, under the control of a promoter active only after the somatic cell has converted to a pluripotent state. A selectable marker gene is used to identify the reprogrammed cells expressing the marker through visible cell selection techniques, such as fluorescent cell sorting techniques. Alternatively, the reprogrammed cells can be produced without a selectable marker. In the examples below, a marker was provided in the genome of the somatic cells downstream of the promoter that regulates Oct-4 expression. The endogenous Oct4 promoter is active in undifferentiated, pluripotent ES cells. A drug-selectable population of Oct-4-expressing ES cells did not persist through the culture period necessary for myeloid differentiation. However, because some Oct-4 expression can persist into early stages of differentiation, it is appropriate to enrich the population for pluripotent cells by selecting colonies having characteristic ES cell morphology and by maintaining the cells under ES cell maintenance culture conditions. It is not intended that all cells in the reprogrammed cell culture have the desired level of potency. Given the inefficiencies of cell sorting technology, the variations in levels of gene expression and other biological effects, some cells in the enriched population may not be pluripotent. However, at a practical level, the reprogrammed cell population derived from somatic cells is enriched for pluripotent cells.

The non-lethal marker can be constructed to enable its subsequent removal using any of a variety of art-recognized techniques, such as removal via Cre-mediated, site-specific gene excision. For example, it may become desirable to delete the marker gene after the pluripotent cell population is obtained, to avoid interference by the marker gene product in the experiment or process to be performed with the cells. Targeted deletions can be accomplished by providing structure(s) near the marker gene that permits its ready excision. That is, a Cre/Lox genetic element can be used. The Lox sites can be built into the cells. If it is desired to remove the marker from the pluripotent cells, the Cre agent can be added to the cells. Other similar systems also can be used. Because Cre/Lox excision can introduce undesirable chromosomal rearrangements and can leave residual genetic material after excision, the inventors recognize the desirability of introducing the potency-determining factors into the somatic cells using non-integrating, episomal vectors and obtaining cells from which the episomal vectors are lost (e.g., at a rate of about 5% per generation) by subsequently withdrawing the drug selection used to maintain the vectors during the reprogramming step.

The following examples are provided as further non-limiting illustrations of methods for identifying potency-determining genes or factors for converting somatic cells into pluripotent cells. In some examples, human H1 Oct4 knock-in ES cells were differentiated in stromal cell co-culture to yield cells suited for use as reprogrammable somatic cells. These cells are a model for cells isolated from a post-natal individual for use in a somatic cell reprogramming method.

The methods were repeated with other differentiated cell types. One cell type was human fetal lung fibroblast cells, IMR-90. See, Nichols W, et al., Science 196:60-63 (1977), incorporated herein by reference as if set forth in its entirety. IMR-90 cells are being extensively characterized by the ENCODE Consortium, are readily available from American Type Culture Collection (ATCC; Manassas, Va.; Catalog No. CCL-186), and have published DNA fingerprints that allow independent confirmation of the origin of reprogrammed clones. In addition, these cells proliferate robustly in Eagle's Minimal Essential Medium—10% FBS for more than twenty passages before undergoing senescence, but grow slowly in human ES cell culture conditions, a difference that provides a proliferative advantage to reprogrammed clones and aids in their selection by morphological criteria alone. Other differentiated cell types used in the methods were human post-natal foreskin fibroblast cells (ATCC; Catalog No. CRL-2097) and human adult skin cells (ATCC; Catalog No. CRL-2106).

The cells were made receptive for transduction with a viral expression system as described below. The somatic cells were transduced with polynucleotides encoding potency-determining factors thought to be associated with pluripotency, such that the somatic cells were reprogrammed to pluripotent cells. It is not yet determined whether all fourteen potency-determining factors provided in transduction vectors were taken up and expressed in the somatic cells. Having identified a set of fourteen potency-determining factors, and a subset of at least two of the fourteen factors, sufficient to reprogram somatic cells, the inventors provide one of ordinary skill in art the with the ability to identify one or more specific subsets of the potency-determining factors that are also capable of somatic reprogramming, thereby facilitating identification of other subsets of such potency-determining factors. Accordingly, the methods described below facilitate the identification of the potency-determining factors involved in reprogramming somatic cells into pluripotent cells.

It is specifically envisioned that the set of potency-determining factors sufficient to reprogram somatic cells can vary with the cell type of the somatic cells. It is noted that exposure to a set of fourteen potency-determining factors resulted in conversion to a pluripotent status in cultures of the indicated somatic cells. As shown below, one can identify a set of potency-determining factors sufficient to reprogram other cell types by repeating the methods described below using different combinations of potency-determining factors, which may include some or all of the fourteen factors as well as other potency-determining factors. Consequently, one can produce pluripotent cell lines/populations that are substantially genetically identical to a pre-existing, differentiated, somatic cell.

EXAMPLES

In the following examples, differentiated cells received vectors that encoded various potency-determining factors. Some of the cells contained in their genome a marker gene that encodes EGFP positioned downstream from the regulated Oct4 promoter, which is active only in pluripotent cells. The production of this useful tool is described in Yu et al., supra, which demonstrated that differentiated cells can become pluripotent via cell-cell fusion with human ES cells.

Example 1

Lentiviral Vector Packaging and Production

Transgene-expressing lentivirus vector was produced in 293FT cell lines (Invitrogen). 293T is a fast-growing, highly transfectable clonal variant derived from transformed 293 embryonal kidney cells, which contains the large T antigen for high-level expression of the packaging proteins that contribute to higher viral titers. For routine maintenance and expansion, these cells were cultured in 293FT medium (DMEM/10% FBS, 2 mM L-glutamine and 0.1 mM MEM Non-Essential Amino Acids) in the presence of 500 µg/ml geneticin. For packaging, 293FT cells were collected by trypsinization. Following removal of trypsin by centrifugation, these cells were aliquoted into T75 flasks ($15 \times 10^6$ cells/flask, and 6 flasks per construct) in 293FT medium without geneticin.

Co-transfection of lentiviral vector and two helper plasmids was carried out with Superfect® transfection reagent (Qiagen) immediately following cell aliquoting (lentiviral vector:MD.G:pCMVdeltaR8.9:Superfect®=5 µg:5 µg:10 µg:40 µl in 400 µl of Iscove's Modified Dulbecco's Medium (IMDM) (1×)/flask incubated at room temperature for 10 minutes). The next day, the culture medium containing the transfection mixture was replaced with fresh 293FT medium supplemented with 1 mM sodium pyruvate (8 ml/flask). Lentivirus-containing supernatant was collected around 48 to 72 hours after transduction (~48 ml per construct). The 293FT cell debris was removed from the supernatant by centrifugation at 3000 rpm (1750 g) for 15 minutes at 4° C. To concentrate the lentivirus, the supernatant was filtered through 0.4 µM cellulose acetate (CA) membrane (Cornington, 115 ml low-protein binding), and ultracentrifuged in 70 ml sterilized bottles (Beckman, Cat#355622, polycarbonate for 45Ti rotor only) at 33,000 rpm (50,000 g) for 2.5 hours at 4° C. Lentivirus along with any remaining cell debris formed a visible pellet at the bottom of the centrifuge tube. Following supernatant removal, PBS (~300 µl for each construct) was added to resuspend the pellet by rocking the centrifuge tubes at 4° C. for 8 to 14 hours, or at room temperature for 2 hours. The remaining cell debris was removed by centrifugation at 5000 rpm (2700 g) for 5 minutes, and the resuspended lentivirus was aliquoted and stored at −80° C. The titer obtained generally ranged between $10^7$ to $10^8$ viral particles (vp)/ml after concentration. The sequence for a lentivirus (pSIN4-EF2-Stella-puro; SEQ ID NO:6, with the sequence for Stella from 3604 to 4083) harboring Stella (SEQ ID NO:1) is provided in the Sequence Listing. The same sequence was used for all other potency-determining factors (e.g., SEQ ID NOS: 2-5), except that the sequence for Stella (SEQ ID NO:1) was replaced with the sequence of another potency-determining factor.

Figure 4A:
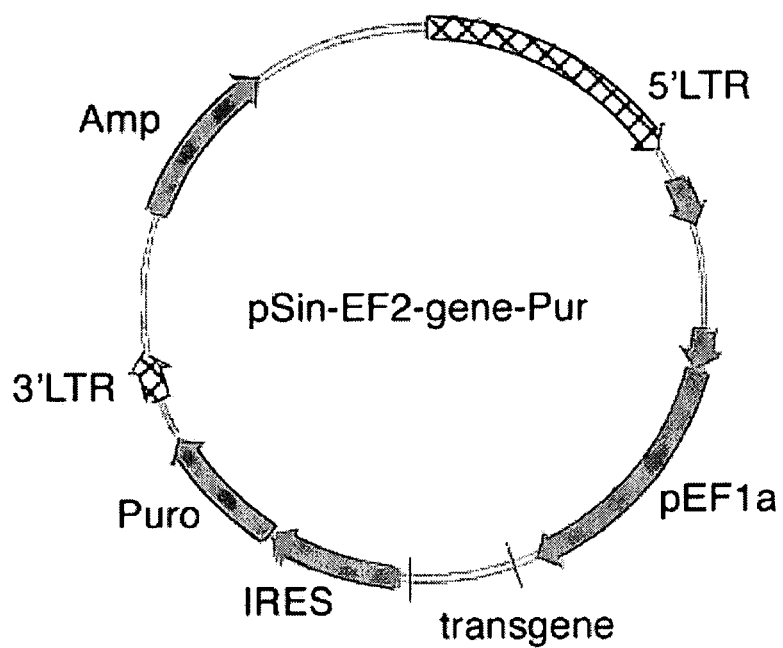
FIGS. 4A-C illustrate lentiviral transduction of somatic cells.
Figure 4B:
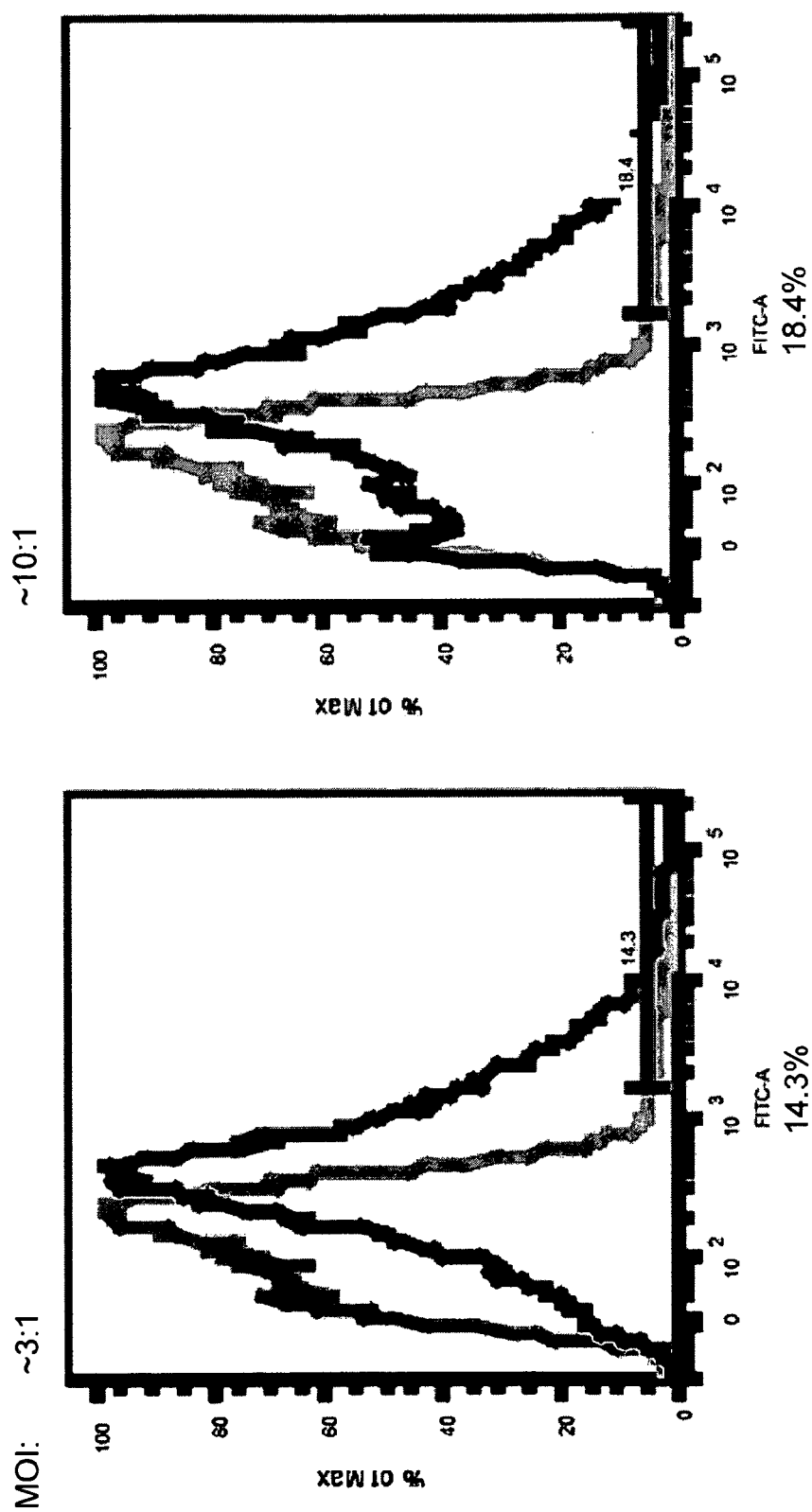

To efficiently introduce potency-determining factors into myeloid cells, inventors modified the lentiviral expression system (FIG. 4A). Inventors reduced the size of the original lentiviral construct (>11 kb) by removing sequences neighboring 5' and 3' LTRs through serial deletion analysis. These modifications minimized the negative effect on the packaging efficiency. The titer obtained routinely ranged between $10^5$ to $10^6$ vp/ml of supernatant, and $10^7$ to $10^8$ vp/ml after concentration (through ultracentrifugation). Restriction sites were introduced into the backbone for convenient exchanges of the coding regions for specific transgenes.

Example 2

Figure 2A:
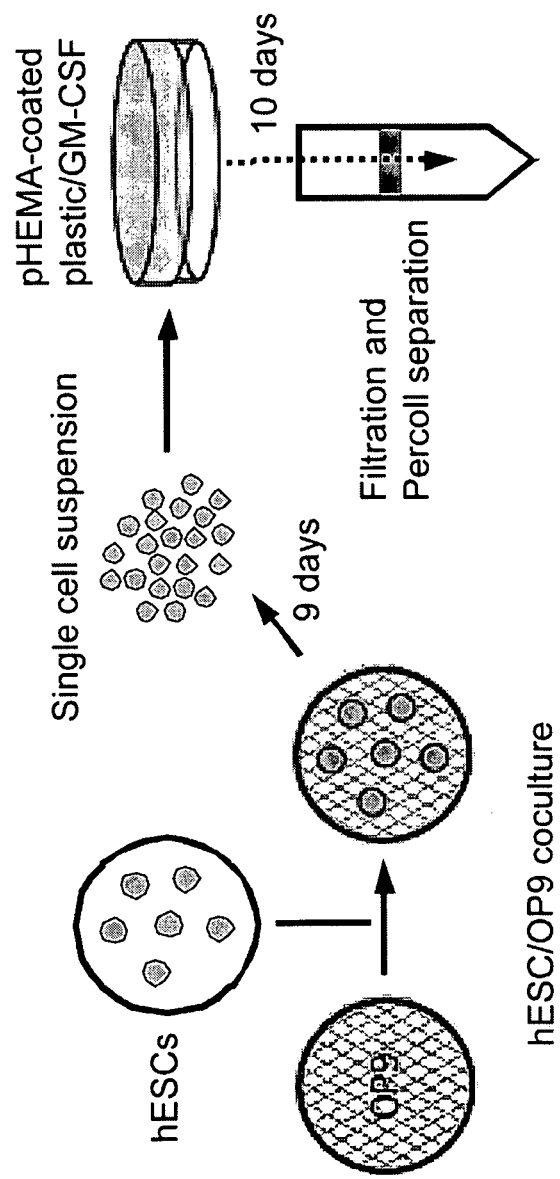
FIGS. 2A-B illustrate human H1 ES cell differentiation.

Reprogramming of Myeloid Precursor Cells After Lentiviral Transduction and Expression of Potency-Determining Factors To identify genes capable of reprogramming differentiated cells back to a state of pluripotency, efficient transduction of the cells is required. Inventors first tested the lentiviral transduction efficiency immediately after Percoll® purification of a human H1 Oct4 knock-in ES cells (FIG. 2).

H1.1 human ES cells (WiCell Research Institute; Madison, Wis.) were maintained on irradiated mouse embryonic fibroblasts (MEFs) in DMEM/F12 culture medium consisting of 80% Dulbecco's modified Eagle's medium (no pyruvate, high glucose formulation; Invitrogen; Carlsbad, Calif.) supplemented with 20% KnockOut serum replacer, 1% non-essential amino acids (Gibco), 1 mM L-glutamine, 0.1 mM β-mercaptoethanol (Sigma) and 4 ng/ml basic fibroblast growth factor (bFGF) (all from Invitrogen unless otherwise noted), as previously described (see Amit et al., Dev Biol. 227:271-278 (2000); and Thomson et al., Science 282:1145-1147 (1998), each of which is incorporated herein by reference as if set forth in its entirety). Feeder-free culture on Matrigel® (BD Biosciences; Bedford, Mass.) with chemically defined TeSR™ medium (StemCell Technologies, Inc.) was carried out as described in Ludwig et al. Ludwig T, et al, Nat. Methods. 3:637-646 (2006); and Ludwig T, et al., Nat. Biotechnol. 24:185-187 (2006), each of which is incorporated herein by reference as if set forth in its entirety.

The H1 Oct4 knock-in ES cell line was generated from the H1.1 human ES cells according to a method described by Zwaka & Thomson. U.S. Patent Publication No. 2006/0128018 and Zwaka T & Thomson J, Nat. Biotechnol. 21:319-321 (2003), each of which is incorporated herein by reference as if set forth in its entirety. Briefly, a gene targeting vector was constructed by inserting a cassette, an IRES-EGFP, an IRES-NEO and a simian virus polyadenylation sequence (approximately 3.2 kilobases (kb)) into the 3' untranslated region of the fifth exon of the human Oct-4 (octamer-binding transcription factor 4) gene, also known as POU domain, class 5, transcription factor 1 (POU5F1). This cassette was flanked in the 5' direction by a 6.3 kb homologous arm and by a 1.6 kb (6.5 kb in the alternative targeting vector) homologous arm in the 3' region (FIG. 1). The cassette was inserted at position 31392 of the Oct-4 gene (SEQ ID NO:2). The long arm contained a sequence from 25054-31392. The short arm contained a sequence from 31392-32970. In an alternative targeting vector, the short arm was substituted by a longer homologous region (31392-32970 in AC006047 plus 2387-7337 in gene accession number AC004195). Isogenic homologous DNA was obtained by long-distance, genomic PCR and subcloned. All genomic fragments and the cassette were cloned into the multiple cloning site (MCS) of a cloning vector, pBluescript® SK II (GenBank Accession Number X52328; Stratagene; La Jolla, Calif.).

For electroporation, cells were harvested with collagenase IV (1 mg/ml, Invitrogen) for 7 minutes at 37° C., washed with medium and re-suspended in 0.5 ml culture medium (1.5-$3.0 \times 10^7$ cells). To prepare the cells for electroporation, cells were added to 0.3 ml phosphate-buffered saline (PBS; Invitrogen) containing 40 mg linearized targeting vector DNA. Cells were then exposed to a single 320 V, 200 µF pulse at room temperature using a BioRad Gene Pulser® II (0.4 cm gap cuvette). Cells were incubated for ten minutes at room temperature and were plated at high-density on Matrigel®. G418 selection (50 mg/ml; Invitrogen) was started 48 hours after electroporation. After one week, G418 concentration was doubled. After three weeks, surviving colonies were analyzed individually by PCR using primers specific for the NEO cassette and for the POU5F1 gene just downstream of 3' homologous region, respectively. PCR-positive clones were re-screened by Southern blot analysis using BamHI digested DNA and a probe outside the targeting construct.

Figure 3:
FIG. 3 illustrates the Oct-4 region containing the knock-in construct of FIG. 1.

The H1 Oct4 knock-in ES cell line expressed both EGFP and neomycin phosphotransferase (neo) from an endogenous Oct4 promoter/regulatory region using dual internal ribosome-entry sites (IRES) (FIG. 3). Expression of EGFP and neo in the H1 Oct4 knock-in ES cells indicated an active, endogenous Oct4 promoter/regulatory region.

H1 Oct4 knock-in ES cells were maintained through co-culture with mouse OP9 bone marrow stromal cells (FIG. 2A) maintained on gelatin-coated 10 cm plastic dishes (BD Biosciences) consisting of: DMEM medium (Invitrogen) supplemented with 20% non-heat-inactivated defined fetal bovine serum (FBS; HyClone Laboratories; Logan, Utah) (10 ml/dish). The OP9 cultures were split every 4 days at a ratio of 1:7. For use in human ES cell differentiation, after OP9 cells reached confluence on the fourth day, half of the medium was changed, and the cells were cultured for an additional four days.

Figure 2B:
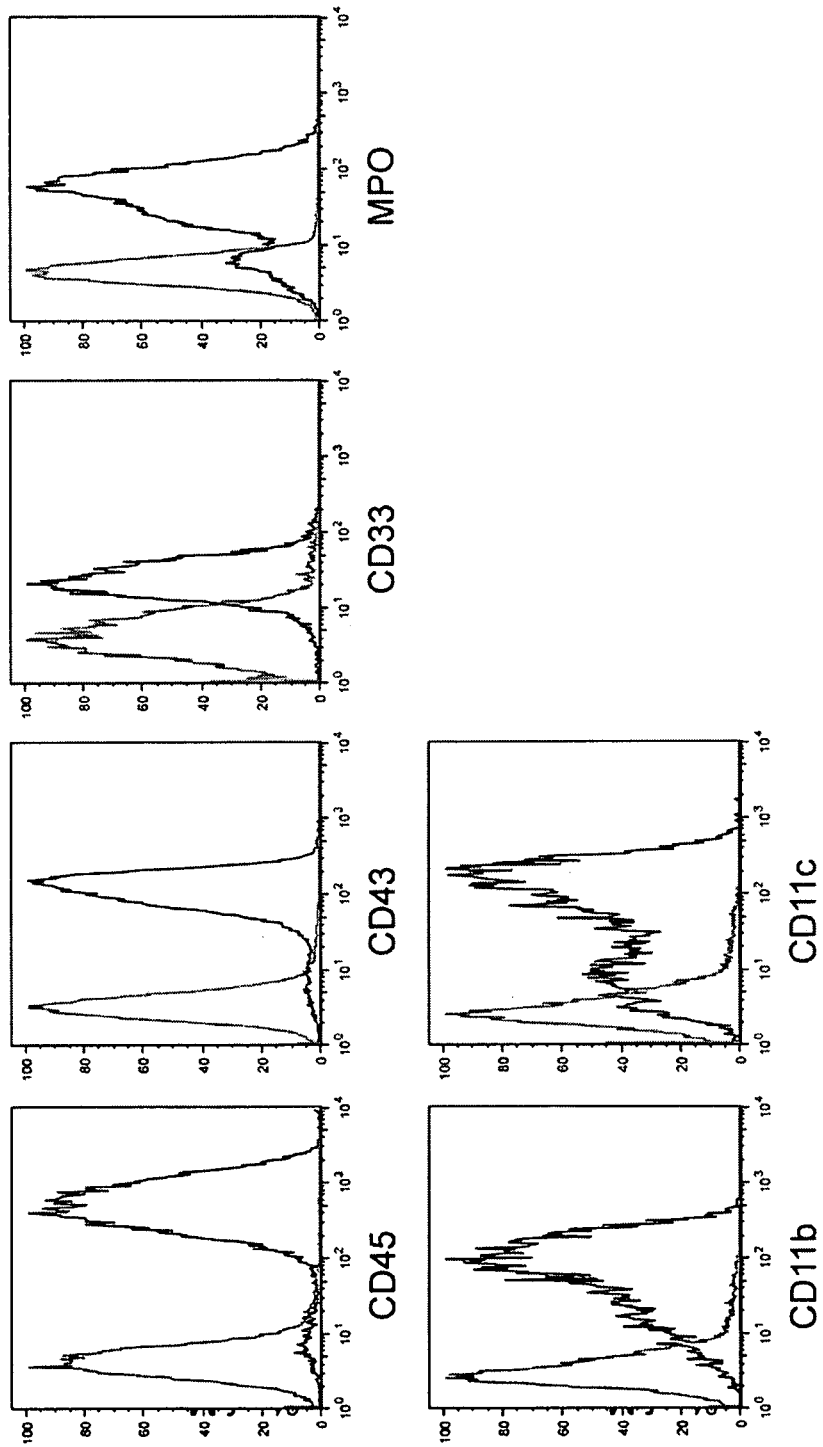

For reprogramming, H1 Oct4 knock-in ES cells were differentiated into attached cells (i.e., CD29+CD44+CD166+ CD105+CD73+CD31−). Briefly, human H1 Oct4 knock-in ES cells (p76 to 110) were added to the OP9 monolayer ($1.5 \times 10^6$/10-cm dish) in 20 ml of DMEM medium supplemented with 10% FBS (HyClone Laboratories) and 100 μM monothioglycerol (MTG; Sigma; St. Louis, Mo.). The human ES/OP9 cell co-culture was incubated for nine days with changes of half of the medium on days 4, 6 and 8. After incubation, the co-culture was dispersed into individual cells by collagenase IV treatment (1 mg/ml in DMEM medium, Invitrogen) for 20 minutes at 37° C., followed by trypsin treatment (0.05% Trypsin/0.5 mM EDTA, Invitrogen) for 15 minutes at 37° C. Cells were washed twice with medium and re-suspended at $2 \times 10^6$/ml in DMEM medium supplemented with 10% FBS, 100 μM MTG and 100 ng/ml GM-CSF (Leukine; Berlex Laboratories Inc.; Richmond, Calif.). Cells were further cultured in flasks coated with poly(2-hydroxyethyl methacrylate) (pHEMA; Sigma) for 10 days with changes of half of the medium every 3 days. During adhesion-preventing pHEMA culture, cells that would otherwise be adherent formed floating aggregates, while the cells of interest grew as individual cells in suspension. Large cell aggregates were removed by filtration through 100 μM cell strainers (BD Biosciences), while small aggregates and dead cells were removed by centrifugation through 25% Percoll® (Sigma). The differentiated cells recovered from the cell pellet expressed CD33, MPO, CD11b and CD11c molecules, which are characteristic for bone marrow myeloid cells (FIG. 2B). Inventors routinely produce $6-10 \times 10^6$ differentiated cells from $1 \times 10^6$ H1 ES cells (human H1 Oct4 knock-in ES cells). See also, Yu J, et al., Science 318:1917-1920 (2007), including the supplemental materials available at the Science website on the World Wide Web, incorporated herein by reference as if set forth in its entirety.

Lentivirus encoding a potency-determining factor (MOI: 3 to 10) was added to the cell culture after addition of polybrene carrier at a final concentration of 6 μg/ml (Sigma). The lentivirus-containing medium was replaced with fresh medium the next day, and cells were cultured further in appropriate medium. Drug selection, if needed, started the third day after transduction. As shown in FIG. 5B, the transduction efficiency was very low (~18.4% at MOI of 10). Moreover, the expression of EGFP was barely above background. Similar results have been obtained with routine plasmid or Epstein-Barr virus nuclear antigen (EBNA)-based plasmid transfections (data not shown).

Figure 4C:
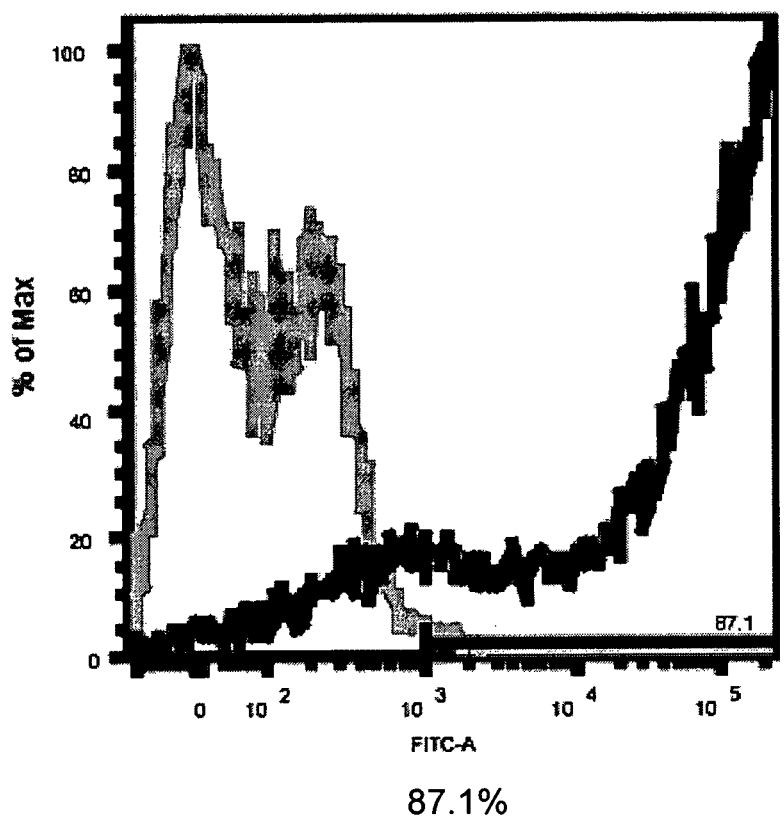

On the other hand, cells having high transduction efficiency were prepared as follows. The Percoll®-purified H1 Oct4 knock-in ES cells were allowed to differentiate further to mesenchymal-like cells for an additional seven days in the presence of GM-CSF on Matrigel®, as described above. Many cells attached to the plate during this culture period. The attached cells (referred to herein below as Oct4KICD45+A cells, or simply as CD45+A cells) showed significantly higher transduction efficiency (FIG. 4C) and were used for this reprogramming experiment. While the cells were not CD45+ at the time of the experiments, the cells were obtained from CD45+ cells. As noted elsewhere herein, cell surface markers on the attached cells were characterized as CD29+, CD44+, CD166+, CD105+, CD73+ and CD31−.

Inventors tested the hypothesis that differentiated cells could be reprogrammed to a state of pluripotency by expressing potency-determining factors in Oct4KICD45+A cells (FIG. 3), and obtained promising results. Because Nanog and Oct-4 are the best characterized potency-determining factors, inventors examined the effect of their over-expression in the cells.

Figure 5:
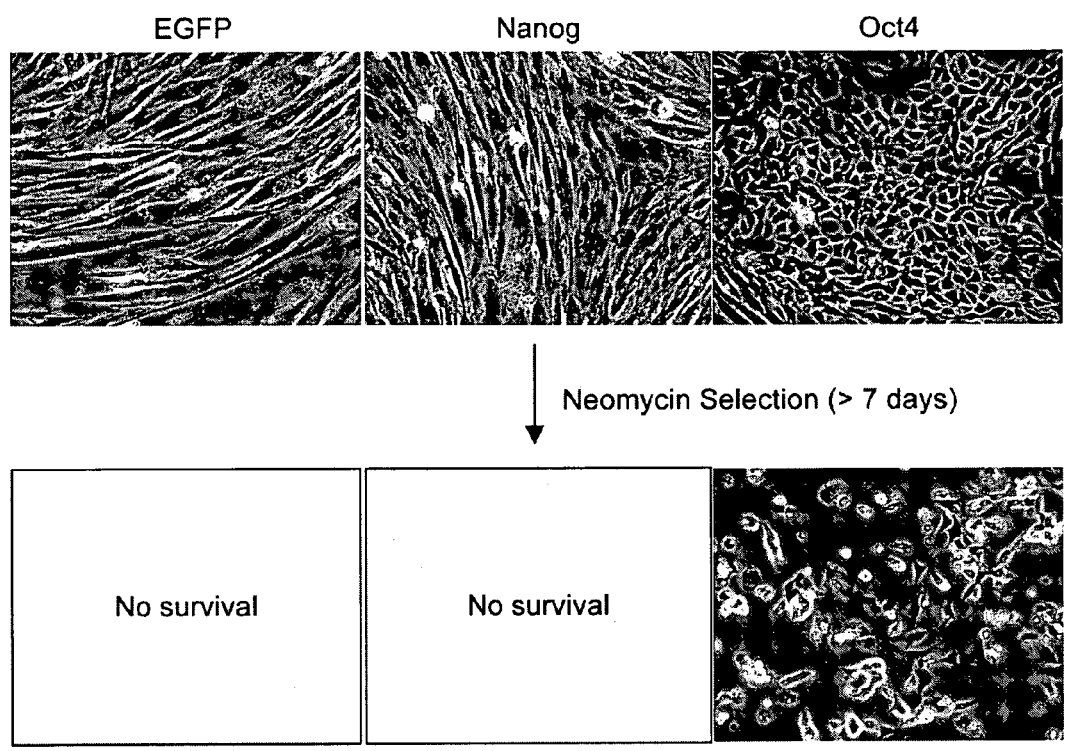
FIG. 5 illustrates transgene overexpression in cells differentiated for seven days on Matrigel®. No significant change in morphology was observed in cells overexpressing Nanog or EGFP (control). Morphology of Oct-4-expressing cells changes dramatically, and many of these cells survived neomycin selection, but none of these cells showed typical human ES cell morphology, indicating that a drug-selectable population of Oct-4-expressing ES cells does not persist through the culture period necessary for myeloid differentiation.

The Oct4KICD45+A cells were first dissociated to individual cells with trypsin and replated onto Matrigel® at ~$10^5$ cells/well of 6-well plates in TeSR™ medium. Transgene-expressing lentiviral transduction was carried out the next day. Nanog-expressing Oct4KICD45+A cells showed similar morphology to that of EGFP transfected cells (FIG. 5). Nanog over-expression, however, significantly enhanced Oct4KICD45+A cell proliferation, similar to that observed in human ES cells. Following neomycin selection for an active endogenous Oct4 promoter/regulatory region, no Nanog- or EGFP-transfected cells survived. Importantly, these results indicate that a drug-selectable population of Oct-4-expressing ES cells does not persist through the culture period necessary for differentiation. Oct-4 expression resulted in dramatic morphological changes (FIG. 5), and many of these cells survived neomycin selection. None of these cells, however, exhibited morphology typical of human ES cells. The Oct4KICD45+A cells co-expressing Nanog and Oct-4 showed morphological changes similar to those observed in cells expressing Oct-4 alone. Thus, it appears that the two key potency-determining factors, Nanog and Oct-4, alone were not sufficient to convert differentiated cells to pluripotency.

Cells were analyzed using cell-sorting methods before and after exposing the somatic cells to the factors. Adherent cells were individualized by trypsin treatment (0.05% Trypsin/0.5 mM EDTA, Invitrogen), and fixed in 2% paraformaldehyde for 20 minutes at room temperature. The cells were filtered through a 40-μm mesh, and resuspended in FACS buffer (PBS containing 2% FBS and 0.1% sodium azide). Cells grown in suspension were stained in the FACS buffer supplemented with 1 mM EDTA and 1% normal mouse serum (Sigma). Intracellular myeloperoxidase (MPO) staining was performed using Fix & Perm® reagents (Caltag Laboratories; Burlingame, Calif.). About 100 μl of cell suspension containing $5 \times 10^5$ cells was used in each labeling. Both primary and secondary antibody incubation (where applied) were carried out at room temperature for 30 minutes. Control samples were stained with isotype-matched control antibodies. After washing, the cells were resuspended in 300-500 µl of the FACS buffer, and analyzed on a FACSCalibur flow cytometer (BDIS; San Jose, Calif.) using CellQuest™ acquisition and analysis software (BDIS). A total of 20,000 events were acquired. All of the antibodies used in the flow cytometry analysis are listed in Table 1. The final data and graphs were analyzed and prepared using FlowJo software (Tree Star, Inc.; Ashland, Oreg.).

TABLE 1

Antibodies for flow cytometry.

| ANTIGEN | LABEL | Clone/Product# | ISOTYPE | VENDOR |
| --- | --- | --- | --- | --- |
| SSEA-3 | None | MAB4303 | ratIgM | Chemicon |
| SSEA-3 | None | 14-8833-80 | ratIgM | eBioscience |
| SSEA-4 | None | MAB4304 | mIgG3 | Chemicon |
| SSEA-4 | APC | FAB1435A | mIgG3 | R&D systems |
| Tra-1-60 | None | MAB4360 | mIgM | Chemicon |
| Tra-1-81 | None | MAB4381 | mIgM | Chemicon |
| CD29 | PE | MCA2298PE | IgG | AbD Serotec |
| Tra-1-85 | APC | FAB3195A | mIgG1 | R&D Systems |
| CD140a | PE | 556002 | mIgG2a | BD Pharmingen |
| CD56 | PE | 340724 | mIgG2b | BDIS |
| CD73 | PE | 550257 | mIgG1 | BD Pharmingen |
| CD105 | PE | MHCD10504 | mIgG1 | Caltag |
| CD31 | FITC | 557508 | mIgG1 | BD Pharmingen |
| CD34 | FITC | 555821 | mIgG1 | BD Pharmingen |

BD Pharmingen (San Diego, CA)
BD Immunocytometry Systems (BDIS) (San Jose, CA)
Caltag Laboratories (Burlingame, CA)
Chemicon International (Temecula, CA)
AbD Serotec (Raleigh, NC)
NA—not applicable.

To further evaluate the potency-determining factors involved in reprogramming these cells, inventors explored the transduction of pools of ES cells enriched with various combinations of potency-determining factors. An exemplary pool of potency-determining factors for reprogramming myeloid precursors included the fourteen potency-determining factors described in Table 2 below.

TABLE 2

Human ES cell-enriched genes.

| GENE SYMBOL | UNIGENE ID | ENTREZ ID | ACCESSION |
| --- | --- | --- | --- |
| POU5F1 (Human Oct-4) | Hs.249184 | 5460 | NM_002701 |
| Sox2 | Hs.518438 | 6657 | NM_003106 |
| Nanog | Hs.329296 | 79923 | NM_024865 |
| FoxD3 | Hs.546573 | 27022 | NM_012183 |
| UTF1 | Hs.458406 | 8433 | NM_003577 |
| Stella | Hs.131358 | 359787 | NM_199286 |
| Rex1 | Hs.335787 | 132625 | NM_174900 |
| ZNF206 | Hs.334515 | 84891 | NM_032805 |
| Sox15 | Hs.95582 | 6665 | NM_006942 |
| Mybl2 | Hs.179718 | 4605 | NM_002466 |
| Lin28 | Hs.86154 | 79727 | NM_024674 |
| DPPA2 | Hs.351113 | 151871 | NM_138815 |
| ESG1 | Hs.125331 | 340168 | NM_001025290 |
| Otx2 | Hs.288655 | 5015 | NM_172337 |

Figure 6A:
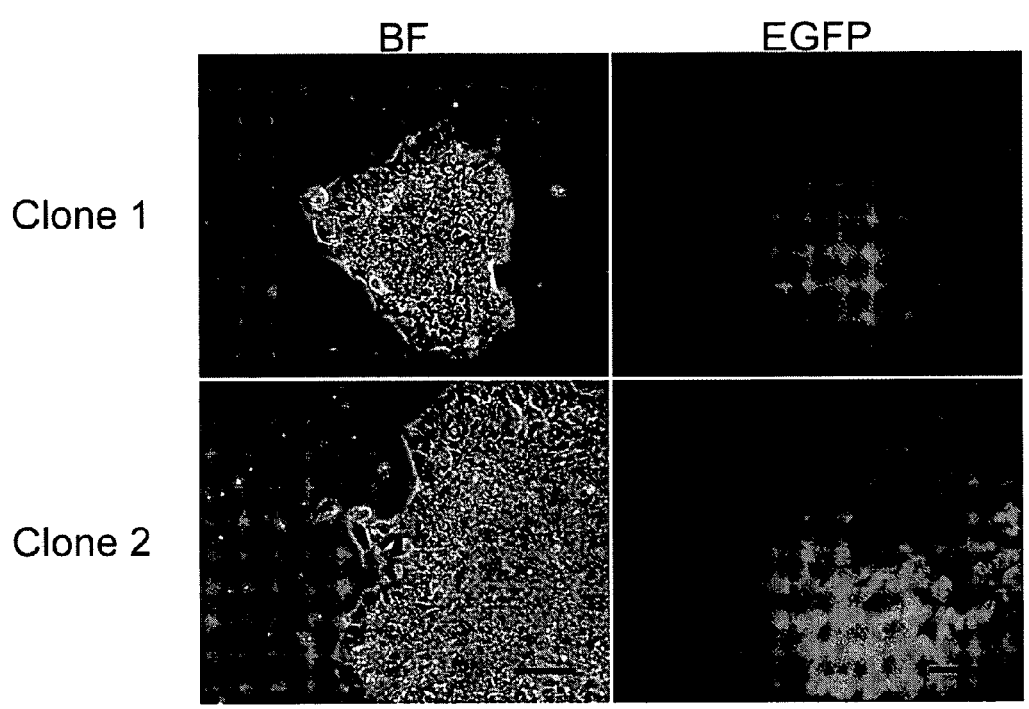
FIGS. 6A-B illustrate reprogramming of Oct4KICD45+A cells through introduction of fourteen potency-determining factors.

The expression of at least some of these fourteen factors in the Oct4KICD45+A cells resulted in colonies with typical morphology of pluripotent cells, such as human ES cells (FIG. 6A—left-hand photos). After neomycin selection from ~$10^5$ starting Oct4KICD45+A cells, over ten colonies having the distinct ES cell morphology initially appeared. More than half of these colonies were subsequently lost to differentiation, suggesting either that over-expression of one or more introduced genes had a negative effect on the cells or that the cells continued to depend upon the foreign transgenes and gene silencing. Nevertheless, surviving colonies expressed the endogenous Oct4 promoter-driven EGFP (FIG. 7A—right-hand photos), indicating that the endogenous Oct4 promoter/regulatory region was reactivated.

Figure 6B:
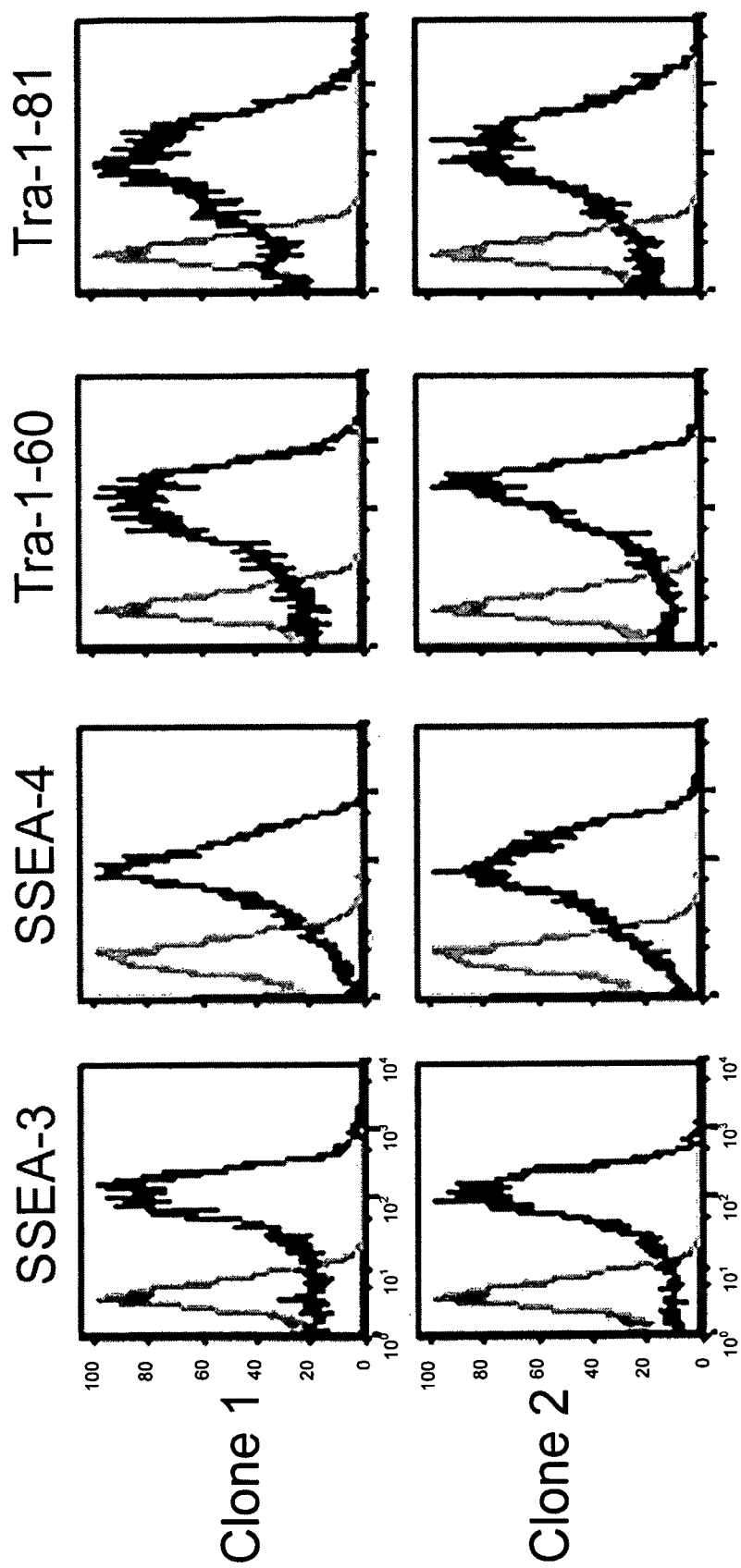

In this embodiment, EGFP expression occurs when the native Oct4 promoter/regulatory region is active. In other words, undifferentiated cells are identified by a green color that disappears when the cells differentiate. Thus, the expression of endogenous Oct-4 in the primate ES cells was selectable. These colonies also expressed Oct-4, SSEA3, SSEA4, Tra-1-60 and Tra-1-81 pluripotent cell-specific markers (FIG. 6B). Similar results were obtained in reprogrammed colonies obtained using chemically defined TeSR™ medium.

Inventors randomly picked six colonies from two separate transfections with the same pool of fourteen ES cell-enriched potency-determining factors, and propagated five stable colonies for at least eight weeks. Thus, inventors identified a novel approach for reprogramming primate somatic cells to become higher potency cells by administering fourteen potency-determining factors into the somatic cells.

When these cells were exposed to other combinations of potency-determining factors (i.e., Sox2, c-Myc, Oct 3/4 and Klf4) using the lentiviral delivery system described herein, reprogramming and conversion of the cells were not observed.

Figure 7A:
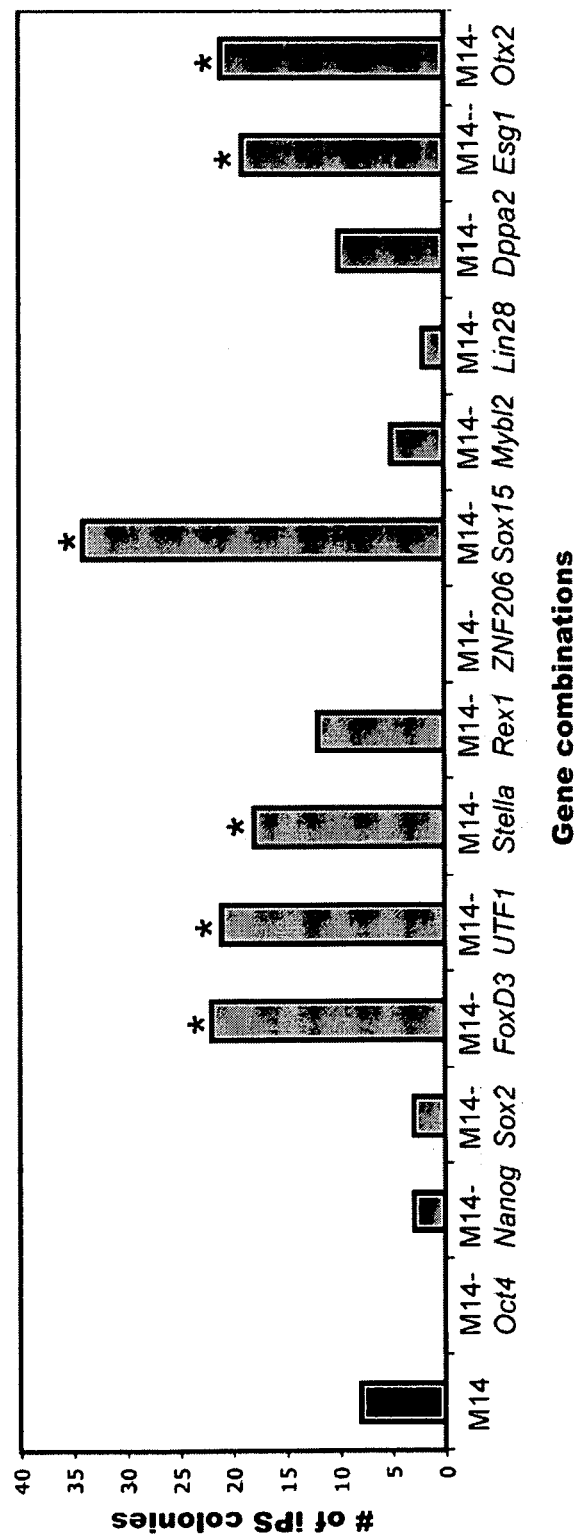
FIGS. 7A-C illustrate reprogramming efficiency, as evidenced by colony formation, after introduction of various sets of potency-determining factors.
Figure 7B:
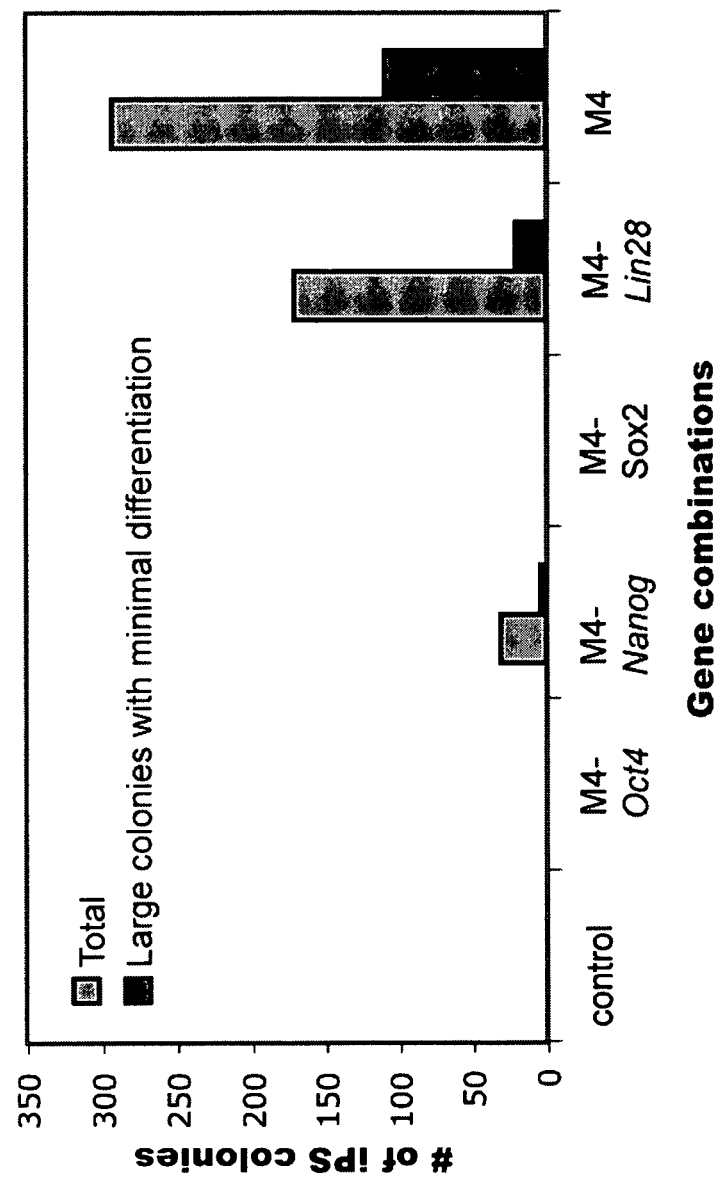

Inventors used the techniques described herein to screen for subsets of the fourteen tested factors that are sufficient to reprogram the tested cells. Inventors' set of fourteen sufficient factors was subsequently narrowed to a set of six, and then four genes sufficient to reprogram these cells (FIGS. 7A-B; described further below). The four genes shown to be sufficient in combination to yield stable pluripotent cell were Oct-4, Nanog, Sox2 and Lin28, as shown in FIG. 7B.

Example 3

Reprogramming of Mesenchymal-Like Cells with a Limited Set of Four Potency-Determining Factors After Lentiviral Transduction To identify a more limited set of potency-determining factors capable of reprogramming differentiated cells back to pluripotency, the above-identified methods were repeated with a combination of Pou5F1 (Oct-4), Nanog, Sox2 and Lin28. Inventors used the techniques described above to screen these potency-determining factors for their ability to reprogram cells.

A different cell type was used in this example to further demonstrate the utility of the methods. The cell type was a mesenchymal-like clonal cell directly differentiated from human H1 Oct4 knock-in ES cells, as described above. As used herein, "clonal" refers to a characteristic of a population of cells derived from a common ancestor (i.e., derived from a single cell, not derived from a cell aggregate). That is, in a "clonal population," the cells display a uniform pattern of cell surface markers and morphological characteristics, as well as being substantially genetically identical.

Briefly, human H1 Oct4 knock-in ES cells (p76 to p110) were induced to differentiate in co-culture with mouse OP9 bone marrow stromal cells. See, Vodyanyk M, et al., Blood 105:617-626 (2005), incorporated herein by reference as if set forth in its entirety. Small aggregates of human H1 Oct4 knock-in ES cells were added to OP9 cells in alpha MEM supplemented with 10% FCS and 100 µM MTG (Sigma). On the next day (day 1) of culture, the medium was changed, and the cultures were harvested on the days indicated below.

On day 2 of co-culture, mesodermal commitment was detected by a peak expression of transcription factors for mesendoderm (GSC, MIXL1 and T (BRACHYURY)) and early mesoderm (EVX1, LHX1 and TBX6) with NimbleGen® (Madison, Wis.) microarrays. During days 3-5, specification of endoderm and mesodermal lineages was observed. This stage was accompanied with sustained expression of genes involved in epithelial-mesenchymal transition (EMT; SNAIL and SLUG) and cell expansion (HOXB2-3). It also coincided with a maximal cell proliferation rate in human H1 Oct4 knock-in ES cells/OP9 co-culture.

Differentiation of specific mesendodermal lineages was observed on days 5-7 of co-culture, when markers of developing endoderm (AFP and SERPINA1), mesenchymal (SOX9, RUNX2 and PPARG2) and hematoendothelial (CDH5 and GATA1) cells were detected. However, muscle-inductive factors (MYOD1, MYF5 and MYF6) were not expressed throughout seven days of co-culture. Moreover, neuroectoderm (SOX1 and NEFL) or trophectoderm (CGB and PLAC) markers were not detected, indicating that OP9 cells provided an efficient inductive environment for directed hESC differentiation toward the mesendodermal pathway.

Also on day 2, a single-cell suspension of the human ES cell-derived cells was harvested by successive enzymatic treatment with collagenase IV (Gibco-Invitrogen) at 1 mg/ml in DMEM/F12 medium for 15 minutes at 37° C. and 0.05% Trypsin—0.5 mM EDTA (Gibco-Invitrogen) for 10 minutes at 37° C. Cells were washed 3 times with PBS—5% FBS, filtered through 70 μM and 30 μM cell strainers (BD Labware; Bedford, Mass.) and labeled with anti-mouse CD29-PE (AbD Serotec; Raleigh, N.C.) and anti-PE paramagnetic monoclonal antibodies (Miltenyi Biotech; Auburn, Calif.). The cell suspension was purified with magnet-activated cell sorting (MACs) by passing it through a LD magnetic column attached to a Midi-MACS separation unit (Miltenyi Biotech) to obtain a negative fraction of OP9-depleted, human H1 Oct4 knock-in ES cell-derived cells. Purity of human H1 Oct4 knock-in ES cell-derived cells was verified using pan antihuman TRA-1-85 monoclonal antibodies (R&D Systems; Minneapolis, Minn.).

Purified human H1 Oct4 knock-in ES cell-derived cells were plated at density of $2 \times 10^4$ cells/ml on semisolid, serum-free medium composed of StemLine™ serum-free medium (Sigma) supplemented with 5-100 ng/ml basic fibroblast growth factor (bFGF; PeproTech; Rocky Hill, N.J.) and 1% methylcellulose (StemCell Technologies, Inc.) with or without 10-20 ng/ml PDGF-BB (PeproTech). PDGF-BB improved growth of mesenchymal cells, but was not essential for colony formation. After 14-21 days of culture, large, compact mesenchymal colonies formed, resembling embryoid bodies (EBs). Mesenchymal colonies were detected on day 7; however, 14-21 days were required to reveal actively growing colonies.

Individual mesenchymal colonies were transferred to wells of a collagen- or fibronectin-coated, 96-well plate pre-filled with 0.2 ml/well StemLine® serum-free medium supplemented with 5-100 ng/ml bFGF. After 3-4 days of culture, adherent cells from individual wells were harvested by trypsin treatment and expanded on collagen- or fibronectin-coated dishes in StemLine® serum-free medium with 5-100 ng/ml bFGF.

Transgene-expressing lentiviral transduction was then carried out as described above. Inventors tested the hypothesis that differentiated mesenchymal-like cells could be reprogrammed to a state of pluripotency by expressing a limited set of potency-determining factors (e.g., Oct-4, Nanog, Sox2 and Lin28). The expression of at least these four potency-determining factors resulted in colonies having cells with typical morphology of pluripotent cells, such as human ES cells (FIG. 7B; dark gray bars). As shown in FIG. 7B, the greatest number of colonies having cells with typical morphology of pluripotent cells was obtained using the full complement of Oct-4, Nanog, Sox2 and Lin28. However, when one of Oct-4, Nanog, Sox2 or Lin28 was absent, the number of ES-like colonies was significantly attenuated (e.g., Nanog or Lin28) or absent (e.g., Oct-4 or Sox2).

In this embodiment, EGFP expression occurred when the native Oct4 promoter/regulatory region was active. In other words, undifferentiated cells were identified by a green color that was absent from differentiated cells. Thus, the expression of endogenous Oct-4 in the cells was selectable. Reprogrammed colonies also expressed Oct-4, SSEA3, SSEA4, Tra-1-60 and Tra-1-81 pluripotent cell-specific markers (data not shown).

Inventors randomly picked six colonies from two separate transfections with the same pool of fourteen ES cell-enriched potency-determining factors, and propagated five stable colonies for at least eight weeks. Thus, inventors identified a novel approach for reprogramming primate somatic cells to become higher potency cells by administering four potency-determining factors into the somatic cells.

When these cells were exposed to other combinations of potency-determining factors (i.e., Sox2, c-Myc, Oct 3/4 and Klf4) using the lentiviral delivery system described herein, reprogramming and conversion of the cells were not observed.

Example 4

Reprogramming of Mesenchymal-Like Cells with a Limited Set of Two Potency-Determining Factors After Lentiviral Transduction To identify an even more limited set of potency-determining factors capable of reprogramming differentiated cells back to pluripotency, the above-identified methods were repeated in the mesenchymal-like cells of Example 3 with a combination of two of the following four potency-determining factors: Oct-4, Nanog, Sox2 and Lin28. Inventors used the techniques described above to screen these potency-determining factors for their ability to reprogram cells.

Figure 7C:
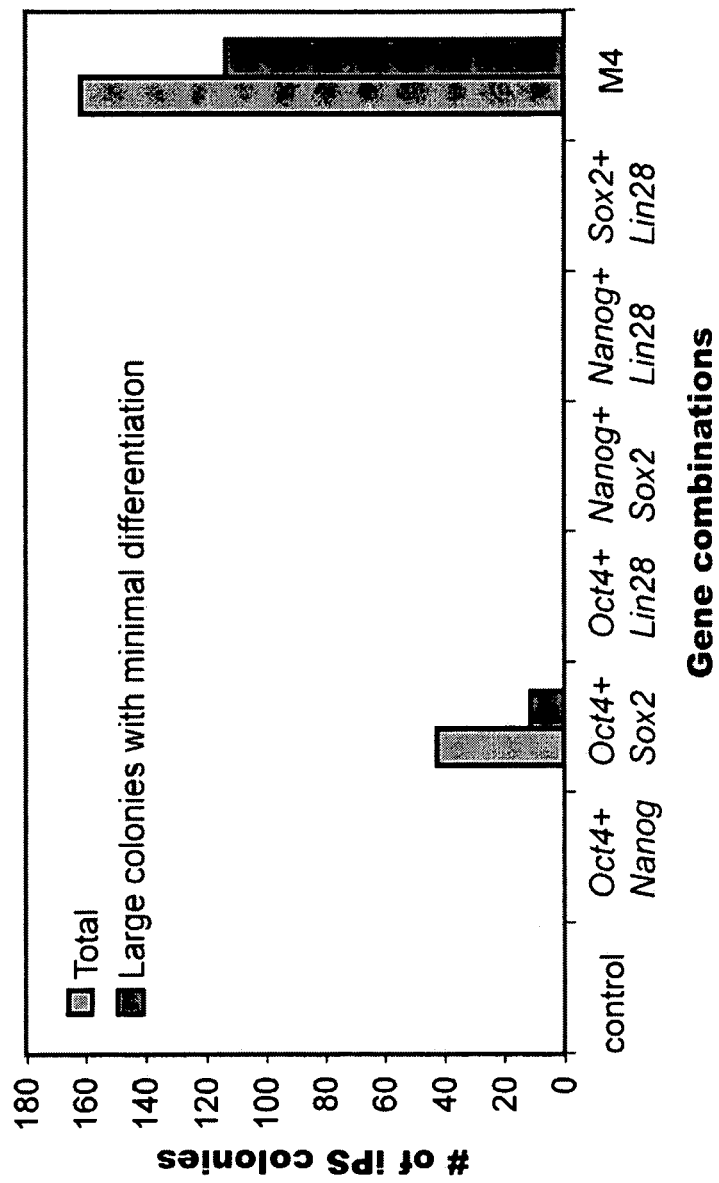

Transgene-expressing lentiviral transduction was then carried out as described above. Inventors tested the hypothesis that differentiated mesenchymal-like cells could be reprogrammed to a state of pluripotency by expressing fewer than four potency-determining factors. The expression of at least Oct-4 and Sox2 (FIG. 7C) resulted in colonies having cells with typical morphology of pluripotent cells, such as human ES cells. Nanog and Lin28, singly and in combination, had a beneficial effect in clone recovery by improving reprogramming efficiency in human ES cell-derived mesenchymal cells to a state of pluripotency, but were essential neither for the initial appearance of reprogrammed cells nor for the expansion of reprogrammed cells.

Example 5

Reprogramming of a Differentiated Cells After Lentiviral Transduction and Expression of Four Potency-Determining Factors To further demonstrate the utility of the limited set of potency-determining factors in reprogramming differentiated cells back to pluripotency, the above-identified methods were repeated with ATCC Catalog No. CCL-186 (IMR-90; ATCC), which are human fetal lung fibroblast cells (see also, Birney E, et al., Nature 447:799-816 (2007)).

Transgene-expressing lentiviral transduction was carried out as described above. That is, IMR-90 cells ($0.9 \times 10^6$/well), were transduced with a combination of Oct-4, Sox2, Nanog and Lin28. Inventors tested the hypothesis that differentiated fibroblast cells could be reprogrammed to a state of pluripotency by expressing a limited set of potency-determining factors (e.g., Oct-4, Sox2, Nanog and Lin28). Following transduction, cells were transferred to three 10-cm dishes seeded with irradiated mouse embryonic fibroblasts (MEFs). By day 12 post-transduction, small colonies with human ES cell morphology became visible. On day 20 post-transduction, a total of 198 colonies were visible on 3 plates. Forty-one of the colonies were picked, thirty-five of which were successfully expanded for an additional three weeks. Six of these colonies were then selected for continued expansion and analysis, and the other twenty-nine were frozen.

The introduction of at least Oct-4, Sox2, Nanog and Lin28 resulted in colonies with typical morphology of pluripotent cells like human ES cells that had a normal karyotype. Cells from each colony likewise expressed telomerase activity and expressed human ES cell-specific surface antigens (i.e., SSEA-3, SSEA-4, Tra-1-60 and Tra1-81). For each of the colonies, the expression of endogenous OCT4 and NANOG was at levels similar to that of pluripotent cells, although the exogenous expression of these genes did vary. Moreover, EB and teratoma formation demonstrated that the reprogrammed cells had a developmental potential to give rise to differentiated derivatives of all three primary germ layers.

DNA fingerprint analysis confirmed that these colonies were derived from IMR-90 cells and that they were not derived from human ES cells lines (e.g., H1, H7, H9, H13 and H14).

Similar to the data obtained with differentiated mesenchymal cells, the greatest number of colonies having cells with typical morphology of pluripotent cells, such as human ES cells was obtained using the full complement of Oct-4, Nanog, Sox2 or Lin28. However, when Oct-4, Nanog, Sox2 or Lin28 were absent, the number of ES-like colonies was significantly attenuated (e.g., Nanog or Lin28) or absent (e.g., Oct-4 or Sox2).

The colonies selected for expansion and detailed characterization proliferated for at least twelve weeks and retained typical characteristics of normal pluripotent cells, even though no selection for the activation of a pluripotency-specific gene was applied during reprogramming.

Reprogrammed cells were identified based on morphology alone (i.e., having a compact colony with high nucleus to cytoplasm ratio and prominent nucleolus). Reprogrammed cells also expressed Oct-4, SSEA3, SSEA4, Tra-1-60 and Tra-1-81 pluripotent cell-specific markers.

Example 6

Reprogramming of Differentiated Cells After Lentiviral Transduction and Expression of Three Potency-Determining Factors To further demonstrate the utility of the limited set of potency-determining factors in reprogramming differentiated cells back to pluripotency, the above-identified methods were repeated with the IMR-90 cells, described above. In this set of experiments, fewer potency-determining factors were used than in Example 5.

Transgene-expressing lentiviral transduction was carried out as described above. IMR-90 cells were transduced with a combination of three of the following: Oct-4, Sox2, Nanog and Lin28. Inventors tested the hypothesis that differentiated fibroblast cells could be reprogrammed to a state of pluripotency by expressing the even more limited set of potency-determining factors. The expression of at least three factors resulted in colonies with typical morphology of pluripotent cells like human ES cells. Reprogrammed colonies having cells with typical morphology of pluripotent cells were obtained using the full complement of Oct-4, Sox2 and Nanog with or without Lin28. Therefore, the presence or absence of Lin28 did not affect reprogramming. However, when any of Oct-4, Nanog or Sox2 was absent, the number of reprogrammed colonies was significantly attenuated or absent.

To examine for the presence of Oct-4, Sox2, Nanog and Lin28 provirus in the reprogrammed cells, PCR with transgene-specific primer pairs (see, Table 3; one gene-specific primer and one lentiviral vector-specific primer) was carried out using genomic DNA from IMR-90 clones as template. The reactions employed the pfx DNA polymerase (Invitrogen, amplification buffer was used at 2×, and enhancer solution was used at 3×), and the following conditions: initial denaturation for 1 minute at 95° C.; 35 cycles of 94° C. for 30 seconds, 55° C. for 30 seconds, 68° C. for 2 minutes; and followed by 68° C. for 7 minutes. PCR analysis for the transgenes showed that either all four transgenes or three transgenes (i.e., Oct-4, Sox2 and Nanog) integrated into the pluripotent cells following exposure to transgene-expressing lentivirus vectors.

TABLE 3

Primer sets for assessing provirus integration.

| Genes | Size (bp) | | Sequences (5' to 3') |
|---|---|---|---|
| OCT4 | 656 | OCT4-F1 | CAGTGCCCGAAACCCACAC (SEQ ID NO: 7) |
| | | SP3 | AGAGGAACTGCTTCCTTCACGACA (SEQ ID NO: 8) |
| NANOG | 732 | NANOG-F2 | CAGAAGGCCTCAGCACCTAC (SEQ ID NO: 9) |
| | | SP3 | AGAGGAACTGCTTCCTTCACGACA (SEQ ID NO: 8) |
| SOX2 | 467 | SOX2-F1 | TACCTCTTCCTCCCACTCCA (SEQ ID NO: 10) |
| | | SP3 | AGAGGAACTGCTTCCTTCACGACA (SEQ ID NO: 8) |
| LIN28 | 518 | LIN28-F1 | AAGCGCAGATCAAAAGGAGA (SEQ ID NO: 11) |
| | | SP3 | AGAGGAACTGCTTCCTTCACGACA (SEQ ID NO: 8) |
| OCT4endo | 113 | OCT4-F2 | AGTTTGTGCCAGGGTTTTTG (SEQ ID NO: 12) |
| | | OCT4-R2 | ACTTCACCTTCCCTCCAACC (SEQ ID NO: 13) |

Reprogrammed cells were identified based on morphology alone (i.e., having a compact colony with high nucleus to cytoplasm ratio and prominent nucleolus). Reprogrammed cells also expressed Oct-4, SSEA3, SSEA4, Tra-1-60 and Tra-1-81 pluripotent cell-specific markers.

Example 7

Reprogramming of Differentiated Cells After Lentiviral Transduction and Expression of Three Potency-Determining Factors To further demonstrate the utility of the limited set of potency-determining factors in reprogramming differentiated cells to pluripotency, the above-identified methods were repeated with ATCC Catalog No. CRL-2097 (ATCC), which are human post-natal foreskin fibroblast cells.

Transgene-expressing lentiviral transduction was carried out as described above. Post-natal fibroblast cells ($0.6 \times 10^6$/well) were transduced with a combination of Oct-4, Sox2, Nanog and Lin28. Inventors tested the hypothesis that differentiated, post-natal, fibroblast cells could be reprogrammed to a state of pluripotency by expressing a limited set of potency-determining factors and obtained promising results. Following transduction, cells were transferred to three 10-cm dishes seeded with irradiated MEFs. By day 15 post-transduction, small colonies with pluripotent cell morphology became visible. On day 20 post-transduction, a total of 57 colonies were visible on the plates. Twenty-nine of the colonies were picked, twenty-seven of which were successfully expanded for an additional three weeks. Four of these colonies were then selected for continued expansion and analysis, and the other twenty-three were frozen.

The expression of Oct-4, Sox2, Nanog and Lin28 resulted in colonies having cells with typical morphology of pluripotent cells, such as human ES cells, and a normal karyotype. Reprogrammed colonies likewise expressed telomerase activity and expressed pluripotent cell-specific markers (i.e., SSEA-3, SSEA-4, Tra-1-60 and Tra1-81). For each, endogenous OCT4 and NANOG was expressed at levels similar to that observed in human pluripotent cells, although the exogenous expression of these genes varied. Moreover, EB and teratoma formation demonstrated that the reprogrammed cells had a developmental potential to give rise to differentiated derivatives of all three primary germ layers. However, in contrast to the iPS cells obtained from IMR-90 cells, iPS cells derived from CRL-2097 cells showed a variation in the lineages apparent in teratomas examined at five weeks. Two of the iPS cell colonies showed neural differentiation; whereas the other two colonies showed multiple foci of columnar epithelial cells, reminiscent of primitive ectoderm.

DNA fingerprint analysis confirmed that these colonies were derived from the original cell line and confirmed that they were not derived from human ES cells lines (e.g., H1, H7, H9, H13 and H14).

Similar to the data obtained after transduction of differentiated mesenchymal cells, the greatest number of colonies having cells with typical morphology of human pluripotent cells were obtained using the full complement of Oct-4, Sox2, Nanog and Lin28. Interestingly, one cell line lacked Lin28, confirming that Lin28 was not essential for reprogramming somatic cells.

The colonies selected for expansion and detailed characterization proliferated for at least twelve weeks and retained typical characteristics of normal human pluripotent cells, even though no selection for the activation of a pluripotency-specific gene was applied during reprogramming.

Reprogrammed cells were identified based on morphology alone (i.e., having a compact colony with high nucleus to cytoplasm ratio and prominent nucleolus). Reprogrammed cells also expressed Oct-4, SSEA3, SSEA4, Tra-1-60 and Tra-1-81 pluripotent cell-specific markers.

When these cells were exposed to other combinations of factors (i.e., Sox2, c-Myc, Oct 3/4 and Klf4) using the lentiviral delivery system described herein, reprogramming and conversion of the cells were not observed.

Example 8

Reprogramming of Differentiated Cells After Lentiviral Transduction and Expression of Four Potency-Determining Factors To further demonstrate the utility of the limited set of potency-determining factors in reprogramming differentiated cells to pluripotency, the above-identified methods were repeated with ATCC Catalog No. CRL-2106 (SK46; ATCC), which are human adult skin cells.

Transgene-expressing lentiviral transduction was carried out as described above. That is, skin cells ($2.0 \times 10^5$/well) were transduced with a combination of Oct-4, Sox2, Nanog and Lin28. Inventors tested the hypothesis that adult skin cells could be reprogrammed to a state of pluripotency by expressing a limited set of potency-determining factors and obtained promising results. Following transduction, cells were transferred to three 10-cm dishes seeded with irradiated mouse embryonic fibroblasts (MEFs). After 10 days in human ES cell culture medium human ES cell culture medium conditioned with irradiated MEFs was used to support cell growth. By day 18 post-transduction, small colonies with pluripotent cell morphology became visible.

Figure 8A:
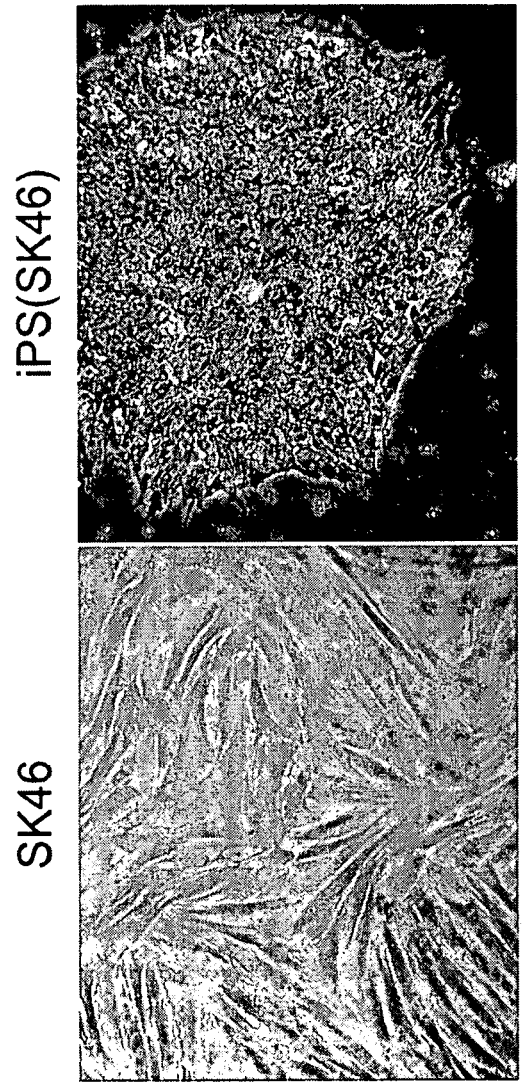
FIGS. 8A-B illustrate reprogramming in human adult skin fibroblasts.
Figure 8B:
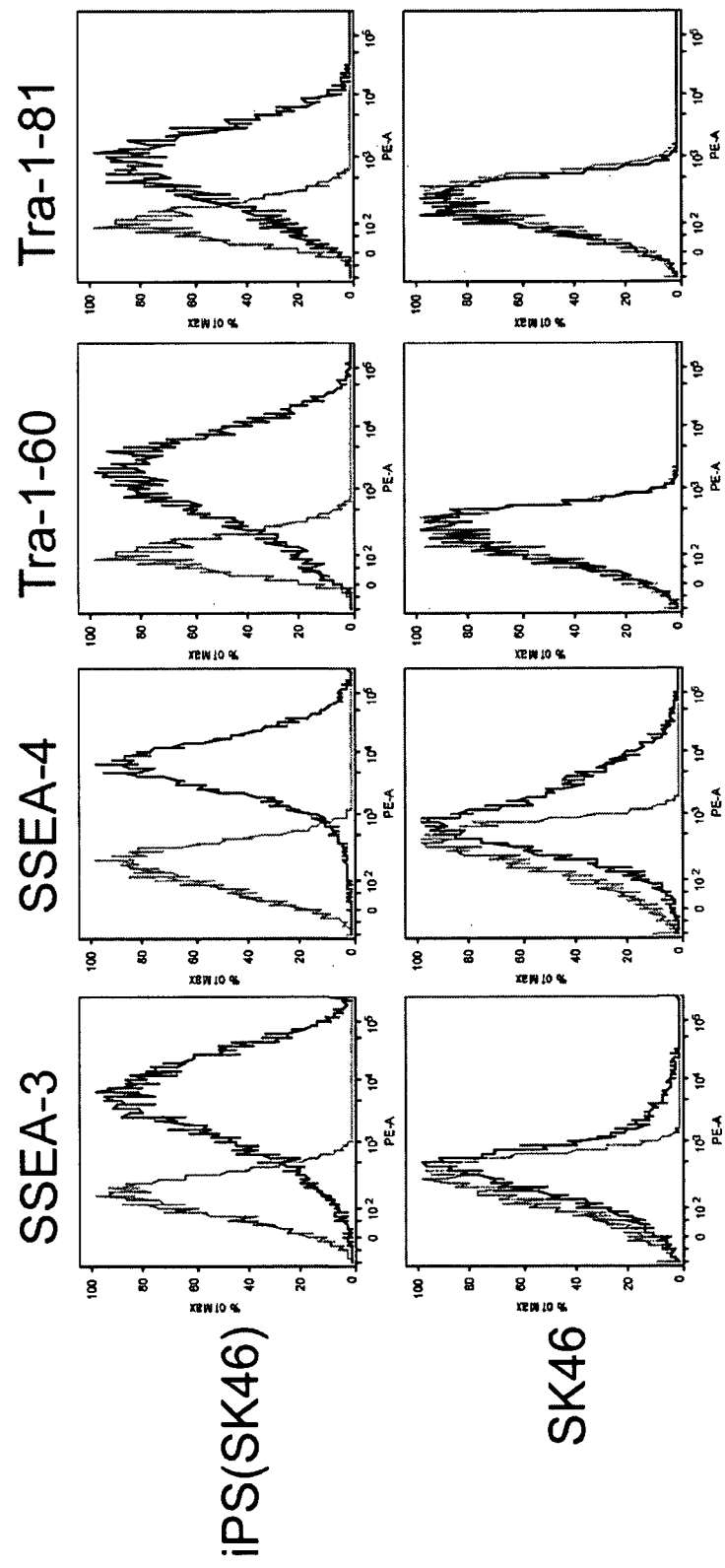

The expression of Oct-4, Sox2, Nanog and Lin28 resulted in colonies having cells with typical morphology of pluripotent cells (see, FIG. 8A), such as human ES cells (i.e., having a compact colony with high nucleus to cytoplasm ratio and prominent nucleolus). As shown in FIG. 8B, the reprogrammed cells also expressed cell surface markers typical of pluripotent cells; SK46 cells (control), however, did not. However, the reprogrammed colonies from adult skin cells appeared later than the cells in Example 7 and had a lower reprogramming efficiency than the cells in Example 7.

Example 9

Increasing Reprogramming Efficiency by Linking Potency-Determining Factors on a Single Construct To increase the reprogramming efficiency, the above-identified methods were repeated using the construct shown in FIG. 4A; however, either Oct-4 or Sox2 were inserted in the transgene section, and Sox2 optionally replaced the puromycin resistance gene. The constructs were then expressed either in 293FT cells or in OCT4 knock-in human H1 ES cells (p6).

Transgene-expressing lentiviral transduction was carried out as described above. That is, 293FT cells or mesenchymal cells (~$2 \times 10^5$ cells/well of 6-well plate, seeded overnight) were transduced with various transgene combinations. Cells were transferred to 10 cm MEF dish (1 well of 6-well plate to $1 \times 10$ cm MEF dish) following the overnight incubation with lentivirus. Geneticin selection (50 µg/ml) for an active, endogenous, OCT4 promoter was carried out between day 11 to 15 post transduction. iPS colonies were counted on day 16.

Figure 9:
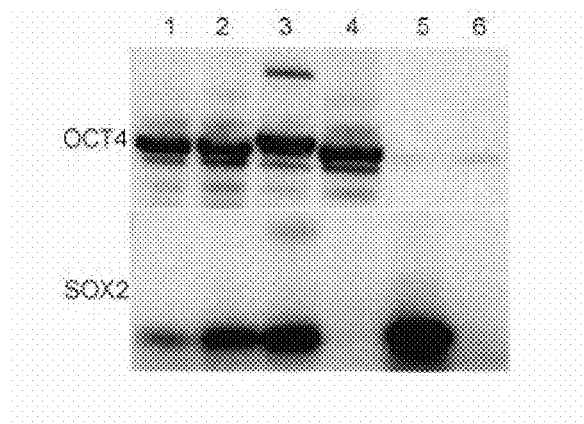
FIGS. 9A-B illustrate the effect on reprogramming of relative expression of Oct-4 and Sox2.
Figure 9:
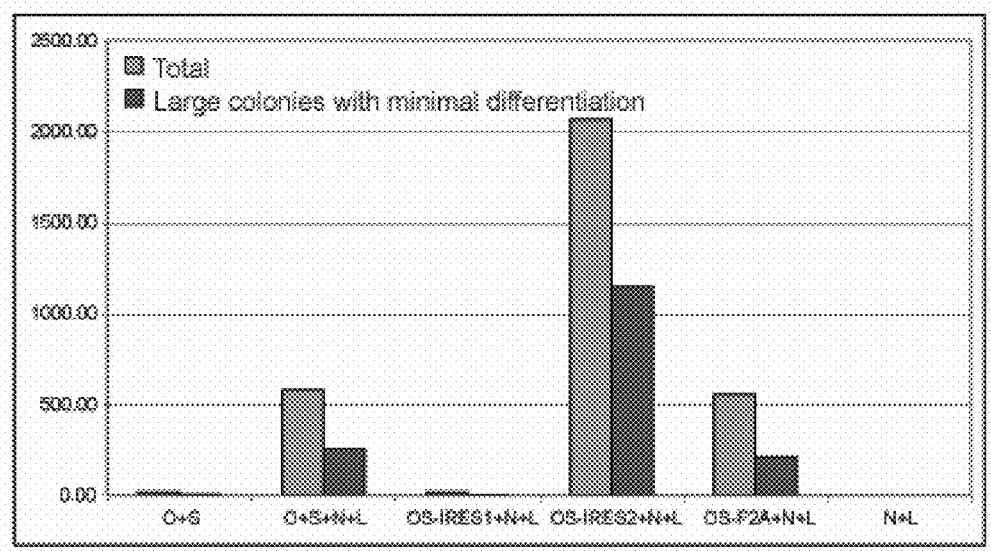

FIG. 9A demonstrates that Oct-4 and Sox2 expression occurred in 293FT cells following transfection (see, e.g., lanes 1-3). In FIGS. 9A-B, pSin4-EF2-Oct4-IRES1-Sox2 is abbreviated as OS-IRES1; pSin4-EF2-Oct4-IRES2-Sox2 is abbreviated as OS-IRES2; pSin4-EF2-Oct4-F2A-Sox2 is abbreviated as OS-F2A; pSin4-EF2-Oct4-IRES1-puro is abbreviated as O; and pSin4-EF2-Sox2-IRES1-puro is abbreviated as S.

FIG. 9B shows that reprogramming efficiency increased in mesenchymal cells derived from OCT4 knock-in human H1 ES cells (p6) when Oct-4 and Sox2 were provided on the same construct (IRES1 is a very low-efficiency internal ribosome entry site; whereas IRES2 is a high-efficiency internal ribosome entry site). OS-IRES2+N+L (the high-efficiency IRES) showed an approximate four fold increase in reprogramming efficiency when compared to O+S, O+S+N+L or OS-IRES1 (the low-efficiency IRES)+N+L. Therefore, providing the potency-determining factors in one construct that provides for approximately equal expression levels of each can improve reprogramming efficiency.

It is understood that certain adaptations of the invention described in this disclosure are a matter of routine optimization for those skilled in the art, and can be implemented without departing from the spirit of the invention, or the scope of the appended claims.

All publications and patents mentioned in the above specification are herein incorporated by reference. Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come within the scope of the following claims.

We claim:

1. A method of reprogramming primate somatic cells, the method comprising the steps of:
   introducing a retroviral vector encoding a plurality of potency-determining factors into the primate somatic cells under conditions sufficient to reprogram the cells, wherein the potency-determining factors comprise Oct-4 and Sox2, and do not comprise c-Myc and Klf4; and
   culturing the primate somatic cells under embryonic stem cell culture conditions to obtain pluripotent reprogrammed cells.

2. The method of claim 1, wherein the primate somatic cells are obtained from a post-natal individual.

3. The method of claim 1, wherein the primate somatic cells are obtained by in vitro differentiation of a stem cell.

4. The method of claim 1, wherein the retroviral vector is a lentiviral vector.

5. The method of claim 1, wherein the potency-determining factors are introduced to the somatic cells as a reprogramming sequence in which a nucleic acid sequence encoding the potency-determining factor is operably linked to a heterologous promoter.

6. The method of claim 1, wherein the potency-determining factors are Oct-4, Sox2, and at least one of Nanog and Lin28.

7. The method of claim 1, wherein the potency-determining factors are Oct-4 and Sox2.

8. The method of claim 1, wherein the reprogrammed cells (i) express a cell marker selected from the group consisting of Oct-4, SSEA3, SSEA4, Tra-1-60 and Tra-1-81; (ii) exhibit morphology characteristic of pluripotent cells; and (iii) form teratomas when introduced into an immunocompromised animal.

9. A method of reprogramming primate somatic cells, the method comprising the steps of:
   introducing a retroviral vector encoding a plurality of potency-determining factors into the primate somatic cells under conditions sufficient to reprogram the cells, wherein the potency-determining factors comprise Oct-4, Sox2, Nanog, and Lin28; and
   culturing the primate somatic cells under embryonic stem cell culture conditions to obtain reprogrammed cells having a higher potency level than the primate somatic cells.

* * * * *

SEQUENCE LISTING

```
<160> NUMBER OF SEQ ID NOS: 13

<210> SEQ ID NO 1
<211> LENGTH: 480
<212> TYPE: DNA
<213> ORGANISM: Homo sapiens
<220> FEATURE:
<221> NAME/KEY: misc_feature
<222> LOCATION: (1)..(480)
<223> OTHER INFORMATION: Stella

<400> SEQUENCE: 1
atggacccat cacagtttaa tccaacctac atcccagggt ctccacaaat gctcaccgaa      60
gaaaattccc gggacgattc aggggcctct caaatctcct ccgagacgtt gataaagaac     120
cttagtaact tgactatcaa cgctagtagc gaatctgttt ccctctatc ggaagcttta      180 ctccgtcgag agtctgtagg agcagcagtc ctcagggaaa tcgaagatga gtggctttac     240
agcaggagag gagtaagaac attgctgtct gtgcagagag aaaagatggc aagattgaga     300
tacatgttac tcggcggagt tcgtacgcat gaaagaagac caacaaacaa ggagcctaag     360
ggagttaaga aggaatcaag accattcaaa tgtccctgca gtttctgcgt gtctaatgga     420
tgggatcctt ctgagaatgc tagaataggg aatcaagaca ccaagccact tcagccataa     480

<210> SEQ ID NO 2
<211> LENGTH: 1083
<212> TYPE: DNA
<213> ORGANISM: Homo sapiens
<220> FEATURE:
<221> NAME/KEY: misc_feature
<222> LOCATION: (1)..(1083)
<223> OTHER INFORMATION: Oct-4

<400> SEQUENCE: 2
atggcgggac acctggcttc ggatttcgcc ttctcgcccc ctccaggtgg tggaggtgat      60
gggccagggg ggccggagcc gggctgggtt gatcctcgga cctggctaag cttccaaggc     120
cctcctggag ggccaggaat cgggccgggg gttgggccag gctctgaggt gtgggggatt     180 ccccatgcc ccccgccgta tgagttctgt gggggatgg cgtactgtgg gccccaggtt      240
ggagtggggc tagtgcccca aggcggcttg gagacctctc agcctgaggg cgaagcagga     300
gtcggggtgg agagcaactc cgatgggggcc tccccggagc cctgcaccgt caccctggt     360 gccgtgaagc tggagaagga gaagctggag caaaacccgg aggagtccca ggacatcaaa     420
gctctgcaga aagaactcga gcaatttgcc aagctcctga agcagaagag gatcaccctg     480
```

| | |
|---|---|
| ggatatacac aggccgatgt ggggctcacc ctgggggttc tatttgggaa ggtattcagc | 540 |
| caaacgacca tctgccgctt tgaggctctg cagcttagct tcaagaacat gtgtaagctg | 600 |
| cggcccttgc tgcagaagtg ggtggaggaa gctgacaaca atgaaaatct tcaggagata | 660 |
| tgcaaagcag aaaccctcgt gcaggcccga aagagaaagc gaaccagtat cgagaaccga | 720 |
| gtgagaggca acctggagaa tttgttcctg cagtgcccga acccacact gcagcagatc | 780 |
| agccacatcg cccagcagct tgggctcgag aaggatgtgg tccgagtgtg gttctgtaac | 840 |
| cggcgccaga agggcaagcg atcaagcagc gactatgcac aacgagagga ttttgaggct | 900 |
| gctgggtctc ctttctcagg gggaccagtg tcctttcctc tggccccagg gccccatttt | 960 |
| ggtaccccag gctatgggag ccctcacttc actgcactgt actcctcggt cccttttccct | 1020 |
| gagggggaag cctttccccc tgtctccgtc accactctgg gctctcccat gcattcaaac | 1080 |
| tga | 1083 |

<210> SEQ ID NO 3
<211> LENGTH: 954
<212> TYPE: DNA
<213> ORGANISM: Homo sapiens
<220> FEATURE:
<221> NAME/KEY: misc_feature
<222> LOCATION: (1)..(954)
<223> OTHER INFORMATION: Sox2

<400> SEQUENCE: 3

| | |
|---|---|
| atgtacaaca tgatggagac ggagctgaag ccgccgggcc cgcagcaaac ttcgggggc | 60 |
| ggcggcggca actccaccgc ggcggcggcc ggcggcaacc agaaaaacag cccggaccgc | 120 |
| gtcaagcggc ccatgaatgc cttcatggtg tggtcccgcg gcagcggcg caagatggcc | 180 |
| caggagaacc ccaagatgca caactcgag atcagcaagc gcctgggcgc cgagtggaaa | 240 |
| cttttgtcgg agacggagaa gcggccgttc atcgacgagg ctaagcggct gcgagcgctg | 300 |
| cacatgaagg agcacccgga ttataaatac cggccccggc ggaaaaccaa gacgctcatg | 360 |
| aagaaggata gtacacgct gcccggcggg ctgctggccc ccggcggcaa tagcatggcg | 420 |
| agcggggtcg gggtgggcgc cggcctgggc gcggcgtga accagcgcat ggacagttac | 480 |
| gcgcacatga acggctggag caacggcagc tacagcatga tgcaggacca gctgggctac | 540 |
| ccgcagcacc cgggcctcaa tgcgcacggc gcagcgcaga tgcagcccat gcaccgctac | 600 |
| gacgtgagcg ccctgcagta caactccatg accagctcgc agacctacat gaacggctcg | 660 |
| cccacctaca gcatgtccta ctcgcagcag ggcaccctg catggctct ggctccatg | 720 |
| ggttcggtgg tcaagtccga ggccagctcc agccccctg tggttacctc ttcctcccac | 780 |
| tccagggcgc cctgccaggc cggggacctc cgggacatga tcagcatgta tctcccggc | 840 |
| gccgaggtgc cggaacccgc cgcccccagc agacttcaca tgtcccagca ctaccagagc | 900 |
| ggcccgtgc ccggcacggc cattaacggc acactgcccc tctcacacat gtga | 954 |

<210> SEQ ID NO 4
<211> LENGTH: 630
<212> TYPE: DNA
<213> ORGANISM: Homo sapiens
<220> FEATURE:
<221> NAME/KEY: misc_feature
<222> LOCATION: (1)..(630)
<223> OTHER INFORMATION: Lin28

<400> SEQUENCE: 4

| | |
|---|---|
| atgggctccg tgtccaacca gcagtttgca ggtggctgcg ccaaggcggc agaagaggcg | 60 |

```
cccgaggagg cgccggagga cgcggcccgg gcggcggacg agcctcagct gctgcacggt    120
gcgggcatct gtaagtggtt caacgtgcgc atggggttcg gcttcctgtc catgaccgcc    180
cgcgccgggg tcgcgctcga cccccagtg  gatgtctttg tgcaccagag taagctgcac    240
atggaagggt tccggagctt gaaggagggt gaggcagtgg agttcacctt taagaagtca    300
gccaagggtc tggaatccat ccgtgtcacc ggacctggtg gagtattctg tattgggagt    360
gagaggcggc caaaaggaaa gagcatgcag aagcgcagat caaaaggaga caggtgctac    420
aactgtggag gtctagatca tcatgccaag gaatgcaagc tgccacccca gcccaagaag    480
tgccacttct gccagagcat cagccatatg gtagcctcat gtccgctgaa ggcccagcag    540
ggccctagtg cacagggaaa gccaacctac tttcgagagg aagaagaaga aatccacagc    600
cctaccctgc tcccggaggc acagaattga                                     630

<210> SEQ ID NO 5
<211> LENGTH: 918
<212> TYPE: DNA
<213> ORGANISM: Homo sapiens
<220> FEATURE:
<221> NAME/KEY: misc_feature
<222> LOCATION: (1)..(918)
<223> OTHER INFORMATION: Nanog

<400> SEQUENCE: 5
atgagtgtgg atccagcttg tccccaaagc ttgccttgct ttgaagcatc cgactgtaaa     60
gaatcttcac ctatgcctgt gatttgtggg cctgaagaaa actatccatc cttgcaaatg    120
tcttctgctg agatgcctca cacggagact gtctctcctc ttccctcctc catggatctg    180
cttattcagg acagccctga ttcttccacc agtcccaaag caaacaacc  cacttctgca    240 gagaatagtg tcgcaaaaaa ggaagacaag gtcccagtca agaaacagaa gaccagaact    300
gtgttctctt ccacccagct gtgtgtactc aatgatagat tcagagaca  gaaataccct    360 agcctccagc agatgcaaga actctccaac atcctgaacc tcagctacaa acaggtgaag    420
acctggttcc agaaccagag aatgaaatct aagaggtggc agaaaaacaa ctggccgaag    480
aatagcaatg gtgtgacgca gaaggcctca gcacctacct accccagcct ctactcttcc    540
taccaccagg gatgcctggt gaacccgact gggaaccttc caatgtggag caaccagacc    600
tggaacaatt caacctggag caaccagacc cagaacatcc agtcctggag caaccactcc    660
tggaacactc agaccctggtg cacccaatcc tggaacaatc aggcctggaa cagtccctct    720
tataactgtg gagaggaatc tctgcagtcc tgcatgcagt tccagccaaa ttctcctgcc    780
agtgacttgg aggctgcttt ggaagctgct ggggaaggcc ttaatgtaat acagcagacc    840
actaggtatt ttagtactcc acaaaccatg gatttattcc taaactactc catgaacatg    900
caacctgaag acgtgtga                                                  918

<210> SEQ ID NO 6
<211> LENGTH: 8060
<212> TYPE: DNA
<213> ORGANISM: Artificial Sequence
<220> FEATURE:
<223> OTHER INFORMATION: Lentivirus harboring Stella
<220> FEATURE:
<221> NAME/KEY: misc_feature
<222> LOCATION: (3604)..(4083)
<223> OTHER INFORMATION: Sequence for Stella

<400> SEQUENCE: 6
cggaccgcca ctgccaatta cctgtggttt catttactct aaacctgtga ttcctctgaa     60
```

```
ttattttcat tttaaagaaa ttgtatttgt taaatatgta ctacaaactt agtagttgga      120
agggctaatt cactcccaaa gaagacaaga tatccttgat ctgtggatct accacacaca      180
aggctacttc cctgattagc agaactacac caccagggcca ggggtcagat atccactgac    240
ctttggatgg tgctacaagc tagtaccagt tgagccagat aagtagaag aggccaataa     300 aggagagaac accagcttgt tacaccctgt gagcctgcat gggatggatg acccggagag      360
agaagtgtta gagtggaggt ttgacagccg cctagcattt catcacgtgg cccgagagct     420
gcatccggag tacttcaaga actgctgata tcgagcttgc tacaagggac tttccgctgg     480
ggacttccca gggaggcgtg gcctgggcgg gactggggag tggcgagccc tcagatcctg     540
catataagca gctgcttttt gcctgtactg ggtctctctg gttagaccag atctgagcct     600
gggagctctc tggctaacta gggaacccac tgcttaagcc tcaataaagc ttgccttgag     660
tgcttcaagt agtgtgtgcc cgtctgttgt gtgactctgg taactagaga tccctcagac      720
ccttttagtc agtgtggaaa atctctagca gtggcgcccg aacagggact tgaaagcgaa      780
agggaaacca gaggagctct ctcgacgcag gactcggctt gctgaagcgc gcacggcaag     840
aggcgagggg cggcgactgg tgagtacgcc aaaaattttg actagcggag gctagaagga     900
gagagatggg tgcgagagcg tcagtattaa gcggggggaga attagatcgc gatgggaaaa     960
aattcggtta aggccagggg gaaagaaaaa atataaatta aaacatatag tatgggcaag    1020
cagggagcta gaacgattcg cagttaatcc tggcctgtta gaaacatcag aaggctgtag   1080
acaaatactg ggacagctac aaccatccct tcagacagga tcagaagaac ttagatcatt    1140
atataataca gtagcaaccc tctattgtgt gcatcaaagg atagagataa aagacaccaa    1200
ggaagcttta gacaagatag aggaagagca aaacaaaagt aagaccaccg cacagcaagc    1260
ggccgctgat cttcagacct ggaggaggag atatgaggga caattggaga agtgaattat    1320
ataaatataa agtagtaaaa attgaaccat taggagtagc acccaccaag gcaaagagaa    1380
gagtggtgca gagagaaaaa agagcagtgg gaataggagc tttgttcctt gggttcttgg    1440
gagcagcagg aagcactatg ggcgcagcgt caatgacgct gacggtacag gccagacaat    1500
tattgtctgg tatagtgcag cagcagaaca atttgctgag ggctattgag gcgcaacagc    1560
atctgttgca actcacagtc tggggcatca agcagctcca ggcaagaatc ctggctgtgg    1620
aaagatacct aaaggatcaa cagctcctgg ggatttgggg ttgctctgga aaactcattt    1680
gcaccactgc tgtgccttgg aatgctagtt ggagtaataa atctctggaa cagatttgga    1740
atcacacgac ctggatggag tgggacagag aaattaacaa ttacacaagc ttaatacact    1800
ccttaattga agaatcgcaa aaccagcaag aaaagaatga acaagaatta ttggaattag    1860
ataaatgggc aagtttgtgg aattggttta acataacaaa ttggctgtgg tatataaaat    1920
tattcataat gatagtagga ggcttggtag gtttaagaat agttttttgct gtactttcta    1980 tagtgaatag agttaggcag ggatattcac cattatcgtt tcagacccac ctcccaaccc    2040 cgagggacc cgacaggccc gaaggaatag aagaagaagg tggagagaga cagagacaca   2100
gatccattcg attagtgaac ggatctcgac ggtatcgcca caaatggcag tattcatcca    2160
caatttaaaa agaaagggggg ggattggggg gtacagtgca ggggaaagaa tagtagacat    2220
aatagcaaca gacatacaaa ctaaagaatt acaaaaacaa attacaaaaa ttcaaaattt     2280
tcgggtttat tacagggaca gcagagatcc actttggtcg ataagctttg caaagatgga    2340
taaagtttta aacagagagg aatctttgca gctaatggac cttctaggtc ttgaaaggag    2400
tgggaattgg ctccggtgcc cgtcagtggg cagagcgcac atcgcccaca gtccccgaga    2460
```

```
agttgggggg aggggtcggc aattgaaccg gtgcctagag aaggtggcgc ggggtaaact    2520
gggaaagtga tgtcgtgtac tggctccgcc ttttcccga gggtggggga gaaccgtata    2580
taagtgcagt agtcgccgtg aacgttcttt ttcgcaacgg gtttgccgcc agaacacagg    2640
taagtgccgt gtgtggttcc cgcgggcctg gcctctttac gggttatggc ccttgcgtgc    2700
cttgaattac ttccacctgg ctgcagtacg tgattcttga tcccgagctt cgggttggaa    2760
gtgggtggga gagttcgagg ccttgcgctt aaggagcccc ttcgcctcgt gcttgagttg    2820
aggcctggcc tgggcgctgg ggccgccgcg tgcgaatctg gtggcacctt cgcgcctgtc    2880
tcgctgcttt cgataagtct ctagccattt aaaattttg atgacctgct gcgacgcttt    2940
ttttctggca agatagtctt gtaaatgcgg gccaagatct gcacactggt atttcggttt    3000
ttggggccgc gggcggcgac ggggcccgtg cgtcccagcg cacatgttcg gcgaggcggg    3060
gcctgcgagc gcggccaccg agaatcggac gggggtagtc tcaagctggc cggcctgctc    3120
tggtgcctgg cctcgcgccg ccgtgtatcg ccccgcccctg gcggcaagg ctggcccggt    3180 cggcaccagt tgcgtgagcg gaaagatggc cgcttccgg ccctgctgca gggagctcaa    3240
aatggaggac gcgcgctcg ggagagcggg cgggtgagtc acccacacaa aggaaaaggg    3300
cctttccgtc ctcagccgtc gcttcatgtg actccacgga gtaccgggcg ccgtccaggc    3360
acctcgatta gttctcgagc ttttggagta cgtcgtcttt aggttggggg gaggggtttt    3420
atgcgatgga gtttccccac actgagtggg tggagactga agttaggcca gcttggcact    3480
tgatgtaatt ctccttggaa tttgcccttt ttgagtttgg atcttggttc attctcaagc    3540
ctcagacagt ggttcaaagt tttttcttc catttcaggt gtcgtgagga attcgcgatc    3600
gccatggacc catcacagtt taatccaacc tacatcccag ggtctccaca aatgctcacc    3660
gaagaaaatt cccgggacga ttcaggggcc tctcaaatct cctccgagac gttgataaag    3720
aaccttagta acttgactat caacgctagt agcgaatctg tttcccctct atcggaagct    3780
ttactccgtc gagagtctgt aggagcagca gtcctcaggg aaatcgaaga tgagtggctt    3840
tacagcagga gaggagtaag aacattgctg tctgtgcaga gagaaaagat ggcaagattg    3900
agatacatgt tactcggcgg agttcgtacg catgaaagaa gaccaacaaa caaggagcct    3960
aagggagtta agaaggaatc aagaccattc aaatgtccct gcagtttctg cgtgtctaat    4020
ggatgggatc cttctgagaa tgctagaata gggaatcaag acaccaagcc acttcagcca    4080
taataggttt aaacatcgat ggcctcgaga aagcggccgc ccccacgcgt aaactagttc    4140
gaaggatccg catgcatcta gggcggccaa ttcgcccct ctcctccccc cccccctaac    4200
gttactggcc gaagccgctt ggaataaggc cggtgtgcgt ttgtctatat gtgattttcc    4260
accatattgc cgtctttggg caatgtgagg gcccggaaac ctggccctgt cttcttgacg    4320
agcattccta ggggtctttc ccctctcgcc aaaggaatgc aaggtctgtt gaatgtcgtg    4380
aaggaagcag ttcctctgga agcttcttga agacaaacaa cgtctgtagc gaccccttgc    4440
aggcagcgga accccccacc tggcgacagg tgcctctgcg gccaaaagcc acgtgtataa    4500
gatacacctg caaaggcggc acaaccccag tgccacgttg tgagttggat agttgtggaa    4560
agagtcaaat ggctctcctc aagcgtattc aacaaggggc tgaaggatgc ccagaaggta    4620
ccccattgta tgggatctga tctgggggcct cggtgcacat gctttacatg tgtttagtcg    4680
aggttaaaaa aacgtctagg ccccccgaac cacggggacg tggttttcct ttgaaaaaca    4740
cgatgataag cttgccacaa cccacaagga gacgaccttc catgaccgag tacaagccca    4800
cggtgcgcct cgccacccgc gacgacgtcc cccgggccgt acgcaccctc gccgccgcgt    4860
```

```
tcgccgacta ccccgccacg cgccacaccg tcgacccgga ccgccacatc gagcgggtca    4920
ccgagctgca agaactcttc ctcacgcgcg tcgggctcga catcggcaag gtgtgggtcg    4980
cggacgacgg cgccgcggtg gcggtctgga ccacgccgga gagcgtcgaa gcggggggcgg   5040
tgttcgccga gatcggcccg cgcatggccg agttgagcgg ttcccggctg ccgcgcagc     5100
aacagatgga aggcctcctg gcgccgcacc ggcccaagga gcccgcgtgg ttcctggcca    5160
ccgtcggcgt ctcgcccgac caccagggca agggtctggg cagcgccgtc gtgctccccg    5220
gagtggaggc ggccgagcgc gccggggtgc ccgccttcct ggagacctcc gcgccccgca    5280
acctccccct tctacgagcgg ctcggcttca ccgtcaccgc cgacgtcgag tgcccgaagg   5340
accgcgcgac ctggtgcatg acccgcaagc ccggtgcctg ataataggcg gccgctcgag    5400
acctagaaaa acatggagca atcacaagta gcaatacagc agctaccaat gctgattgtg    5460
cctggctaga agcacaagag gaggaggagg tgggttttcc agtcacacct caggtacctt    5520
taagaccaat gacttacaag gcagctgtag atcttagcca cttttaaaa gaaaaggggg     5580
gactggaagg gctaattcac tcccaacgaa gacaagatct gcttttgct tgtactgggt     5640
ctctctggtt agaccagatc tgagcctggg agctctctgg ctaactaggg aacccactgc    5700
ttaagcctca ataaagcttg ccttgagtgc ttcaagtagt gtgtgcccgt ctgttgtgtg    5760
actctggtaa ctagagatcc ctcagaccct tttagtcagt gtggaaaatc tctagcagta    5820
gtagttcatg tcatcttatt attcagtatt tataacttgc aaagaaatga atatcagaga    5880
gtgagaggcc ttgacattat aatagattta gcaggaattg aactaggagt ggagcacaca    5940
ggcaaagttc tagagctcgc tgatcagcct cgactgtgcc ttctagttgc cagccatctg    6000
ttgtttgccc ctcccccgtg ccttccttga ccctggaagg tgccactccc actgtccttt    6060
cctaataaaa tgaggaaatt gcatcgcatt gtctgagtag gtgtcattct attctggggg    6120
gtggggtggg gcaggacagc aagggggagg attgggaaga caatagcagg catgctgggg    6180
atgcggtggg ctctatggct tctgaggcgg aaagaaccag ctgggggcgc gccctcgag    6240
gccgccatgg tcatagctgt ttgacgtcag gtggcacttt tcggggaaat gtgcgcggaa    6300
cccctatttg tttatttttc taaatacatt caaatatgta tccgctcatg agacaataac    6360
cctgataaat gcttcaataa tattgaaaaa ggaagagtat gagtattcaa catttccgtg    6420
tcgcccttat tcccttttttt gcggcatttt gccttcctgt ttttgctcac ccagaaacgc    6480
tggtgaaagt aaaagatgct gaagatcagt tgggtgcacg agtgggttac atcgaactgg    6540
atctcaacag cggtaagatc cttgagagtt ttcgccccga agaacgtttt ccaatgatga    6600
gcacttttaa agttctgcta tgtggcgcgg tattatcccg tattgacgcc gggcaagagc    6660
aactcggtcg ccgcatacac tattctcaga atgacttggt tgagtactca ccagtcacag    6720
aaaagcatct tacggatggc atgacagtaa gagaattatg cagtgctgcc ataaccatga    6780
gtgataacac tgcggccaac ttacttctga caacgatcgg aggaccgaag gagctaaccg    6840
ctttttttgca caacatgggg gatcatgtaa ctcgccttga tcgttgggaa ccggagctga    6900
atgaagccat accaaacgac gagcgtgaca ccacgatgcc tgtagcaatg caacaacgt     6960
tgcgcaaact attaactggc gaactactta ctctagcttc ccggcaacaa ttaatagact    7020
ggatggaggc ggataaagtt gcaggaccac ttctgcgctc ggcccttccg gctggctggt    7080
ttattgctga taaatctgga gccggtgagc gtgggtctcg cggtatcatt gcagcactgg    7140
ggccagatgg taagccctcc cgtatcgtag ttatctacac gacggggagt caggcaacta    7200
tggatgaacg aaatagacag atcgctgaga taggtgcctc actgattaag cattggtaac    7260
```

```
tgtcagacca agtttactca tatatacttt agattgattt aaaacttcat ttttaattta    7320
aaaggatcta ggtgaagatc cttttttgata atctcatgac caaatcccct taacgtgagt    7380
tttcgttcca ctgagcgtca gaccccgtag aaaagatcaa aggatcttct tgagatcctt    7440 ttttttctgcg cgtaatctgc tgcttgcaaa caaaaaaacc accgctacca gcggtggttt    7500
gtttgccgga tcaagagcta ccaactcttt ttccgaaggt aactggcttc agcagagcgc    7560
agataccaaa tactgtcctt ctagtgtagc cgtagttagg ccaccacttc aagaactctg    7620
tagcaccgcc tacatacctc gctctgctaa tcctgttacc agtggctgct gccagtggcg    7680
ataagtcgtg tcttaccggg ttggactcaa gacgatagtt accggataag gcgcagcggt    7740
cgggctgaac ggggggttcg tgcacacagc ccagcttgga gcgaacgacc tacaccgaac    7800
tgagatacct acagcgtgag cattgagaaa gcgccacgct tcccgaaggg agaaaggcgg    7860
acaggtatcc ggtaagcggc agggtcggaa caggagagcg cacgagggag cttccagggg    7920
gaaacgcctg gtatctttat agtcctgtcg ggtttcgcca cctctgactt gagcgtcgat    7980
ttttgtgatg ctcgtcaggg gggcggagcc tatggaaaaa cgccagcaac gcggcctttt    8040
tacggttcct ggccttttgc                                                 8060

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
cagtgcccga aacccacac                                                     19

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
agaggaactg cttccttcac gaca                                               24

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
cagaaggcct cagcacctac                                                    20

<210> SEQ ID NO 10
<211> LENGTH: 20
<212> TYPE: DNA
<213> ORGANISM: Artificial
<220> FEATURE:
<223> OTHER INFORMATION: Synthetic oligonucleotide

<400> SEQUENCE: 10
tacctcttcc tcccactcca                                                    20

<210> SEQ ID NO 11
<211> LENGTH: 20
<212> TYPE: DNA
```

```
-continued

<213> ORGANISM: Artificial Sequence
<220> FEATURE:
<223> OTHER INFORMATION: Synthetic oligonucleotide

<400> SEQUENCE: 11
aagcgcagat caaaaggaga                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
agtttgtgcc agggtttttg                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
acttcacctt ccctccaacc                                                20
```